United States Patent [19]

Arai et al.

[11] 4,040,835
[45] Aug. 9, 1977

[54] TWO-EQUIVALENT MAGENTA COUPLERS WITH AMIDO COUPLING-OFF GROUPS

[75] Inventors: Atsuaki Arai; Keisuke Shiba; Minoru Yamada; Nobuo Furutachi; Kotaro Nakamura, all of Minami-ashigara, Japan

[73] Assignee: Fuji Photo Film Co., Ltd., Minami-ashigara, Japan

[21] Appl. No.: 590,998

[22] Filed: June 27, 1975

[30] Foreign Application Priority Data

June 27, 1974 Japan .................. 49-73673

[51] Int. Cl.$^2$ .......................... G03C 7/00; G03C 1/40
[52] U.S. Cl. ......................................... 96/56.5; 96/100
[58] Field of Search .................... 96/56.2, 56.5, 100, 96/74; 260/310 A, 309.2, 310 D

[56] References Cited

U.S. PATENT DOCUMENTS

| | | | |
|---|---|---|---|
| 2,829,975 | 4/1958 | Popeck et al. | 96/100 |
| 3,061,432 | 10/1962 | Menzel et al. | 96/100 |
| 3,271,152 | 9/1966 | Hanson | 96/100 |
| 3,369,897 | 2/1968 | Menzel et al. | 96/100 |
| 3,383,214 | 5/1968 | Anderson | 96/56.6 |
| 3,458,315 | 7/1969 | Loria | 96/56.2 |
| 3,615,504 | 10/1971 | Monbaliu et al. | 96/100 |
| 3,615,506 | 10/1971 | Abbott et al. | 96/100 |
| 3,649,278 | 3/1972 | Iwama et al. | 96/100 |
| 3,725,062 | 4/1973 | Anderson et al. | 96/3 |
| 3,728,115 | 4/1973 | Poot et al. | 96/290 |
| 3,733,335 | 5/1973 | Anderson | 96/100 |
| 3,820,990 | 6/1974 | Fix | 96/77 |
| 3,880,658 | 4/1975 | Lestina et al. | 96/100 |
| 3,900,483 | 8/1975 | Fujimatsu et al. | 96/100 |
| 3,930,863 | 1/1976 | Shiba et al. | 96/100 |

Primary Examiner—David Klein
Assistant Examiner—Richard C. Schilling
Attorney, Agent, or Firm—Sughrue, Rothwell, Mion, Zinn and Macpeak

[57] ABSTRACT

A two-equivalent magenta coupler forming magenta dye images in a color photographic material by a coupling reaction with an oxidation product of a primary aromatic amino color developing agent and having the formula (I)

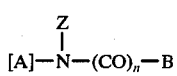

(I)

wherein [A] represents a residue of a magenta dye-forming coupler;

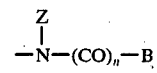

represents a group which is substituted for one of the hydrogen atoms of the active methylene group of the coupler A; Z represents a hydrogen atom, an alkyl group, an aryl group, or a heterocyclic group; B represents a —D-Y residue or an —N⊂Q residue; D represents an oxygen atom, a sulfur atom, or an —NR— group; R of the —NR— group represents a hydrogen atom, an alkyl group, or an aryl group; Y represents an alkyl group, an aryl group, or a heterocyclic group; Q of the —N⊂Q residue represents a non-metal atomic group necessary for forming a 5-membered or 6-membered nitrogen-containing heterocyclic group; $n$ is 1 or 2 and when $n$ is 2, B can also represent a —Y group; a color photographic silver halide light-sensitive material comprising a support having thereon at least one silver halide emulsion layer and containing the two-equivalent magnetic coupler having the formula (I); and an image forming method comprising developing an exposed photographic silver halide light-sensitive material comprising a support having thereon at least one silver halide emulsion layer is the presence of the two-equivalent magenta coupler having the formula (I).

5 Claims, No Drawings

TWO-EQUIVALENT MAGENTA COUPLERS WITH AMIDO COUPLING-OFF GROUPS

DETAILED DESCRIPTION OF THE INVENTION

1. Field of the Invention

The present invention relates generally to color photography and, more particularly, it relates to novel two-equivalent magenta couplers for silver halide color photographic materials. The invention further relates to silver halide color photographic materials containing the novel two-equivalent magenta couplers and also to a color image forming process performed in the presence of the novel two-equivalent magenta couplers.

2. Description of the Prior Art

When a silver halide color photographic material is subjected to color development, the couplers are known to react with the oxidized product of a primary aromatic amino color developing agent to form an indophenol dye, an indoaniline dye, an indamine dye, an azomethine dye, a phenoxazine dye, a phenazine dye, and the like, whereby a color image is formed. A subtractive color process is usually used for color reproduction and, in such a silver halide color photographic material, silver halide emulsions selectively sensitive to blue, green, and red light and yellow, magenta, and cyan dye image-forming agents which are in complementary color relations with them respectively, are used. For forming a yellow color image, an acylacetanilide type coupler or a dibenzoylmethane type coupler is generally used, for forming a magneta color image, a pyrazolone type coupler, a pyrazolobenzimidazole type coupler, a cyanoacetophenone type coupler or an indazolone type coupler is mainly used, and for forming a cyan color image, a phenol type coupler, such as, for instance, a phenol and a naphthol, is mainly used.

In a most preferred embodiment of color photographic materials, couplers for forming dye images are incorporated in the silver halide emulsion layers of color photographic materials. In such a case the couplers incorporated in the emulsion layers must be non-diffusion resistant in the matrix of the emulsion binder.

A majority of conventional couplers for forming dye images or color images are substantially four-equivalent couplers. That is to say, in such four-equivalent couplers the development of 4 moles of silver halide is theoretically required as an oxidizing agent for forming 1 mole of dye by the coupling reaction. On the other hand, in a two-equivalent coupler having an active methylene group substituted with a group which is released as the result of the oxidative coupling thereof with the oxidation product of a primary aromatic amino developing agent, the development of only 2 moles of silver halide is required for forming 1 mole of dye. Thus, since the amount of silver halide required for forming a dye in the case of using a two-equivalent coupler may be 1/2 of the amount required for forming a dye in the case of using a conventional four-equivalent coupler, the use of a two-equivalent coupler provides the advantages that the period of time required for processing the photographic material can be shortened due to the reduction in the thickness of photographic emulsion layers which is possible and also the photographic properties of the developed photographic material are improved by the reduction in the thickness of the photographic layers. In addition, economical advantages due to the reduction of the amount of silver halide required result.

Various attempts have been made for forming two-equivalent couplers from 5-pyrazolone couplers which have hitherto been mainly used as magenta dye forming couplers. For instance, attempts to substitute the 4-position of the pyrazolone ring of a 5-pyrazolone coupler with a thiocyano group as described in U.S. Pat. Nos. 3,214,437 and 3,253,924; with an acyloxy group as described in U.S. Pat. No. 3,311,476; with an aryloxy group as described in U.S. Pat. No. 3,419,391; with a 2-triazolyl group as described in U.S. Pat. No. 3,617,291; and with a halogen atom as described in U.S. Pat. No. 3,522,052 have been made.

However, these 4-position substituted pyrazolone couplers have the disadvantages that these couplers give rise to a large amount of color fog, they sometimes have an inappropriate reactivity, they are converted into non-coupling materials with the passage of time due to the lack of chemical stability of these couplers, and further various difficulties in the synthesis of these couplers occur.

Moreover, formation of a two-equivalent coupler by substituting the 4-position of the 5-pyrazolone with an alkylthio group, an arylthio group, or a heterocyclic thio group as described in U.S. Pat. No. 3,227,554 is also known. However, these conventional thio group-substituted pyrazolone couplers have also the following disadvantages that they exhibit an inappropriate reactivity with the oxidation product of a primary aromatic amino color developing agent, the mercapto compounds released as the result of the coupling reaction have strong photographic actions, which results in making the employment of these couplers in general color photographic materials difficult, and further their chemical stability is insufficient.

On the other hand, in the color photographic system in which couplers are incorporated in a color developer, the use of four-equivalent couplers is disadvantageous since a large amount of silver halide is required for obtaining a desired dye image density and difficulties in the stability of conventional two-equivalent couplers occur.

SUMMARY OF THE INVENTION

Therefore, an object of this invention is to provide a novel two-equivalent magenta coupler substituted at the coupling position of the magenta dye image forming coupler with a group which can be released by the coupling reaction with the oxidation product of a primary aromatic aminocolor developing agent.

A second object of this invention is to provide a novel two-equivalent magenta coupler which has an appropriate reactivity and forms a dye in a high yield without undesirable fog and stains occurring.

A third object of this invention is to provide a color photographic material having a silver halide emulsion layer containing the above-described novel magenta dye image forming coupler.

A fourth object of this invention is to provide a process of improving the sharpness of the color image obtained in the photographic emulsion layer of a color photographic material by using the above-described novel two-equivalent magenta dye image-forming coupler which can be obtained due to the reduction in the amount of silver halide in the photographic emulsion layer.

A fifth object of this invention is to provide a color photographic material capable of providing stable color images by using the novel magenta dye image-forming coupler.

A sixth object of this invention is to provide a two-equivalent magenta coupler which can be easily prepared in a high yield.

A seventh object of this invention is to provide a novel two-equivalent magenta coupler having an improved rate of conversion to a dye, an improved resistance to the reduction in coupling activity due to attack of chemical materials, and an excellent coupling reactivity.

An eighth object of this invention to provide an image-forming process which can be carried out in the presence of the novel two-equivalent magenta coupler substituted at the coupling position of the magenta dye image-forming coupler with a group released by the coupling reaction with the oxidation product of a primary aromatic amino color developing agent.

A ninth object of this invention is to provide an image-forming process in which a silver halide color photographic material is processed with a color developer having incorporated therein the novel two-equivalent magenta coupler substituted at the coupling position of the magenta dye image-forming coupler with a group released by the coupling reaction with the oxidation product of a primary aromatic amino color developing agent.

These and other objects of this invention will become apparent from the following description of the invention.

The above-described various objects of this invention are attained in one embodiment by a two-equivalent magenta coupler represented by the following general formula (I)

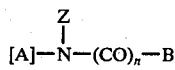

(I)

wherein [A] represents a magenta dye image-forming coupler residue;

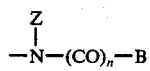

is a group which is substituted for one of the hydrogens of the active methylene group of coupler A; Z represents a hydrogen atom, an alkyl group, an aryl group, or a heterocyclic group; B represents a -D-Y residue or an —N⌒Q residue; D represents an oxygen atom, a sulfur atom, or an -NR- group; R of the —NR—group represents a hydrogen atom, an alkyl group, or an aryl group; Y represents an alkyl group, an aryl group, or a heterocyclic group; Q of the —N⌒Q residue represents a non-metal atomic group necessary for forming a 5-membered or 6-membered nitrogen-containing heterocyclic group; n is 1 or 2; and when n is 2, B can also represent a —Y group.

In a second embodiment the above-described various objects are obtained with a silver halide color photographic material having on a support at least one silver halide emulsion layer and containing the above described two-equivalent magenta coupler represented by the general formula I.

In another embodiment of this invention, these objects are achieved by processing an image-wise exposed silver halide color photographic material with a color developer containing a primary aromatic amino color developing agent in the presence of the above-described two-equivalent magenta coupler represented by the general formula (I).

DETAILED DESCRIPTION OF THE INVENTION

In general formula (I) described above, [A] can be any magenta dye image-forming coupler residue but the residue preferably is a 5-oxo-4-pyrazonyl type group or a 3-pyrazolo-[1,5a]-benzimidazolyl type group.

Particularly useful two-equivalent magenta couplers of this invention are those couplers represented by the following formulae (II) to (V);

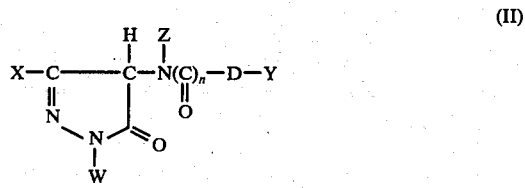

(II)

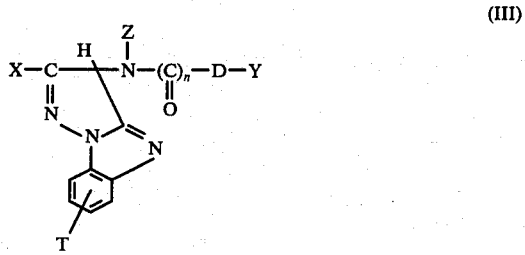

(III)

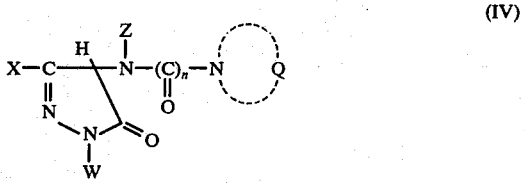

(IV)

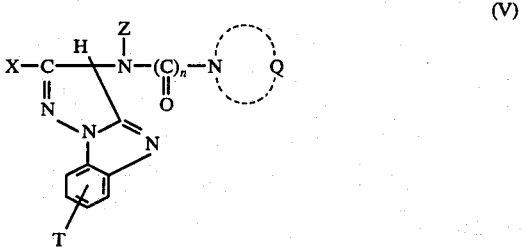

(V)

In the above general formulae, W represents a hydrogen atom; or has up to 40 carbon atoms, preferably up to 22 carbon atoms. Suitable examples of groups for W include a straight chain or branched chain alkyl group (e.g., a methyl, ethyl, isopropyl, tert-butyl, hexyl, dodecyl, docosyl, etc., group), an alkenyl group (e.g., an allyl, β-vinylethyl, etc., group), a cycloalkyl group (e.g., a cyclohexyl, norbornyl, 7,7-dialkylnorbornyl, 2-pentadecyl-7,7-dialkylnorbornyl, etc., group), an aralkyl group (e.g., a benzyl β-phenylethyl, etc., group) or a cycloalkenyl group (e.g., a cyclopentenyl, cyclohexenyl, etc., group) and these groups as described above can be substituted with one or more of a halogen atom (e.g., a chlorine, bromine, fluorine, etc., atom), a nitro group, a cyano group, an aryl group (e.g., a phenyl, tolyl, methoxyphenyl, naphthyl, etc., group), an alkoxy group (e.g., a methoxy, butoxy, octyloxy, etc., group), an aryloxy group (e.g., a phenoxy, tolyloxy, naphthoxy, etc., group), a carboxyl group, an alkylcarbonyl group (e.g., a methylcarbonyl, octylcarbonyl, etc., group), an arylcarbonyl group (e.g., a phenylcarbonyl, tolylcarbonyl, etc., group), an alkoxycarbonyl group (e.g., a methoxycarbonyl, butoxycarbonyl, etc., group), an aryloxycarbonyl group (e.g., a phenoxycarbonyl, tolyloxycarbonyl, etc., group), a sulfo group, an acyloxy group (e.g., an acetyl group, etc.), a sulfamoyl group (e.g., an N-methylsulfamoyl, N,N,-diethylsufamoyl, N-methyl-N-phenylsulfamoyl, etc., group), a carbamoyl group (e.g., an N-ethylcarbamoyl, N-methyl-N-decylcarbamoyl, N-phenylcarbamoyl, etc, group), an acylamino group (e.g., an acetamido, butyramido, benzamido, etc., group), a diacylamino group (e.g., a phthalimido, 3-heptadecylsuccimimido, etc. group), a ureido group (e.g., an ethylureido, phenylureido, chlorophenylureido, etc., group), a thioureido group, (e.g., an ethylthioureido, phenylthioureido, chlorophenylthioureido, etc., group), an alkoxycarbamide group (e.g., a methyloxycarbamido, octoxycarbamido, etc., group), an aryloxycarbamido group (e.g., a phenoxycarbamido group, etc.), an alkylthiocarbamido group (e.g., a methylthiocarbamido, octylthiocarbamido, etc., group), an arylthiocarbamido group (e.g., a phenylthiocarbamido group, etc.), a sulfonamido group (such as an alkylsulfonamido (e.g., methylsulfonamido, ethylsulfonamido, etc.), arylsulfonamido (e.g., phenylsulfonamido, etc.), etc. group), a heterocyclic group (e.g., a 5- or 6-membered heterocyclic group or condensed hetocyclic group containing at least one herero atom selected from nitrogen, oxygen and sulfur atoms, such as furyl, oxazolyl, benzothiazolyl, imidazolyl, etc., group), an arylsulfonyloxy group (e.g., a phenylsulfonyloxy, tolylsulfonyloxy, etc. group), an alkylsulfonyloxy group (e.g., an ethylsulfonyloxy, dedecylsulfonyloxy, etc., group), an arylsulfonyl group (e.g., a phenylsulfonyl, tolylsulfonyl, etc., group), an alkylsulfonyl group (e.g., a methylsulfonyl, octylsulfonyl, etc., group), an arylthio group (e.g., a phenylthio. tolylthio, etc., group), an alkylthio group (e.g., a methylthio, octylthio, dodecylthio, etc., group), an alkylsulfinyl group (e.g., a methysulfinyl, hexylsulfinyl, etc., group), an arylsulfinyl group (e.g., a phenylsulfinyl, tolylsulfinyl, etc., group), an alkylamino group (e.g., a methylamino, butylamino, etc., group), an dialkylamino group (e.g., an N,N-diethylamino, N-methyl-N-decylamino, etc., group), an anilino group (such as an N-alkylanilino (e.g., N-methylanilino etc.), N-arylanilino (e.g., N-phenylanilino etc.), N-acylanilino (e.g., 2-chloro-5-tetradecanamidoanilino, etc.), etc., group), a hydroxyl group, or a mercapto group.

Furthermore W represents an aryl group (e.g., a phenyl or an α-or β-naphthyl group) or an aryl group having one or more substitutents such as an alkyl group (e.g., a methyl, ethyl, octyl, etc., group), an alkenyl group (e.g., an allyl, β-vinylethyl, etc., group), a cycloalkyl group (e.g., a cyclohexyl, norbornyl, 7,7-dialkylnorbornyl, 2-pentadecyl-7,7-dialkylnorbornyl, etc., group), an aralkyl group (e.g., a benzyl, β-phenylethyl, etc., group), an cycloalkenyl group (e.g., a cyclopentenyl, cyclohexenyl, etc., group), a halogen atoms (e.g., a chloring, bromine, fluorine, etc., atom), a nitro group, a cyano group, an aryl group (e.g., a phenyl, tolyl, methoxyphenyl, naphthyl, etc., group), an alkoxy group (e.g., a methoxy, butoxy, octyloxy, etc., group), an aryloxy group (e.g., a phenoxy, tolyloxy, naphthoxy, etc., group), a caboxy group, an alkylcarbonyl group (e.g., a methylcarbonyl, octylcarbonyl, etc. group), an arylcarbonyl group (e.g., a phenylcarbonyl, tolylcarbonyl, etc., group), an alkoxycarbonyl group (e.g., a methoxycarbonyl, butoxycarbonyl, etc., group), an aryloxycarbonyl group (e.g., a phenoxycarbonyl, tolyloxycarbonyl, etc., group), a sulfo group, an acyloxy group (e.g., an acetoxy, etc., group), a sulfamoyl group (e.g., a methylsulfamoyl, diethylsulfamoyl, phenylsulfamoyl, etc. group), a carbamoyl group (e.g., a carbamoyl, N-octadecylcarbamoyl, N,N-dihexylcarbamoyl, N-methyl-N-phenylcarbamoyl, 3-pentadecylphenylcarbamoyl, etc., group), an acylamino group (e.g., an acetamido, butyramido, benzamido, etc., group), a diacylamino group (e.g., a succinimido, phthalimido, hydantoinyl, etc., group), a ureido group (e.g., an ethylureido, phenylureido, chlorophenylureido, etc., group), a thiouredio group (e.g., an ethylthioureido, phenylthioureido, chlorophenylthioureido, etc., group), an alkyloxycarbamido group (e.g., a methoxycarbamido, octoxycarbamido, etc., group), an aryloxycarbamido group (e.g., a phenyloxycarbamido etc., group), an alkylthiocarbamido group (e.g., a methylthiocarbamido, octylthiocarbamido, etc., group), an arylthiocarbamido group (e.g., a phenylthiocarbamido group, etc.), a sulfonamido group (such as an alkylsulfonamido (e.g., methylsulfonamido, ethylsulfonamido, etc.), arylsulfonamido (e.g., phenylsulfonamido, etc.,) etc., group), a heterocyclic group (e.g., a 5- or 6-membered heterocyclic group or condensed heterocyclic group containing at least one herero atom selected from nitrogen, oxygen and sulfur atoms, such as a furyl, oxazolyl, benzothiazolyl, imidazolyl, etc., group), an arylsulfonyloxy group, (e.g., a phenylsulfonyloxy, tolylsulfonylloxy, etc., group), an alkylsulfonyloxy group, (e.g., an ethylsulfonyloxy, dodecylsulfonyloxy, etc. group), an arylsulfonyl group, (e.g., a phenylsulfonyl, tolylsulfonyl, etc., group), an alkylsulfonyl group (e.g., a methylsulfonyl, octylsulfonyl, etc., group), an arylthio group (e.g., phenylthio, tolylthio, etc., group), an alkylthio group, (e.g., a methylthio, octylthio, dodecylthio, etc., group), an alkylsulfinyl group, (e.g., a methylsulfinyl, hexylsulfinyl, etc., group), an arylsulfinyl group, (e.g., a phenylsulfinyl, tolysulfinyl, etc. group), an alkylamino group (e.g., a methylamino, butylamino, etc., group), a dialkylamino group, (e.g., an N,N-diethylamino, N-methyl-N-decylamino, etc., group), an anilino group, an N-alkylanilino group (e.g., an N-methylanilino group, etc.), an N-arylanilino group (e.g., an N-phenylanilino group, etc.), an N-acylanilino group (e.g., a 2-chloro-5-tetra-decanamidoanilino group), etc., a hydroxyl group, and a mercapto group. More preferably W is a phenyl group substituted with an alkyl group, an alkoxy group, or a halogen atom in at least one of the ortho positions because in such case the coupler remaining in the photographic film processed causes less print out due to the action of heat and light.

Still further, W represents also a heterocyclic group (e.g., a 5-membered or 6-membered heterocyclic group containing a nitrogen atom (for example, a pyridyl, quinolyl or pyrrolyl group, substituted with substituents as described above for the aryl group), or two or more nitrogen atoms (for example, a pyrazolyl, benzotriazolyl, tetrazolyl, etc., group), an oxygen atom (for example, an unsubstituted or substituted furyl or benzofuranyl group having a substitutent described above for the aryl group); a sulfur atom (for example, an unsubstituted or substituted thienyl or benzo[b]thienyl group having substituent as described above for the aryl group); and a heterocyclic group containing two or more different hetero-atoms (such as benzoazolyl, benzothiazolyl, and the like).

Moreover, W represents further an acyl group (such as an alkylcarbonyl group (e.g., an acetyl, butyryl, benzoyl, etc., group), a thioacyl group (such as an alkylthiocarbonyl group (e.g., an octylthiocarbonyl, etc., group), an alkylsulfonyl group (e.g., a methylsulfonyl, octylsulfonyl, etc. group), an arylsulfonyl group (e.g., a phenylsulfonyl, tolylsulfonyl, etc., group )), an alkylsulfinyl group (e.g., a methylsulfinyl, hexylsulfinyl, etc., group), an arylsulfinyl group, (e.g., a phenylsulfinyl, tolylsulfinyl, etc., group), a carbamoyl group (such as an alkylcarbamoyl, dialkylcarbamoyl, arylcarbamoyl, etc., (e.g., N-ethylcarbamoyl, N-methyl-N-decylcarbamoyl, phenylcarbamoyl, etc.) group,) or a thiocarbamoyl group (such as an alkylthiocarbamoyl (e.g., ethylthiocarbamoyl, etc.), dialkylthiocarbamoyl (e.g., N-methyl-N-decylthiocarbamoyl, etc.), arylthiocarbamoyl (e.g., phenylthiocarbamoyl, etc.) etc., group).

In the above described formulae, X represents a hydrogen atom, or has up to 40, preferably up to 22, carbon atoms. Suitable examples of groups for X include an alkyl group, an alkenyl group, a cycloalkyl group, an aralkyl group, or a cycloalkenyl group as defined for W, and these groups may be substituted with one or more substituents as illustrated above in regard to the substituted alkyl group of W.

Furthermore, X represents also an aryl group as defined for W or a heterocyclic group as defined for W, each of which may also have one or more of the substituents as illustrated above for W.

Still further, X represents an alkoxycarbonyl group (e.g., a methoxycarbonyl, ethoxycarbonyl, stearyloxycarbonyl, etc. group), an aryloxycarbonyl group (e.g., a phenoxycarboyl α-naphthoxycarbonyl, β-naphthoxycarbonyl, etc. group), an aralkoxycarbonyl group (e.g., a benzyloxycarbonyl etc., group), an alkoxy group (e.g., a methocy, ethoxy, decyloxy, etc., group), an aryloxy group (e.g., a phenoxy, tolyloxy etc., group), an alkylthio group (e.g., an ethylthio, dodecylthio, etc., group), an arylthio group (e.g., a phenylthio, α-naphthylthio, etc. group), a carboxyl group, an acylamino group (e.g., an acetamido, 3-[(2,4-di-tert-amylphenoxy)acetamido]benzamido, etc., group), a diacylamino group (e.g., a phthalimido, 3-heptadecylsuccinimido, etc., group), an N-alkylacylamino group (e.g., a N-methylpropionamido, etc. group), an N-arylacylamino group (e.g., a N-phenylacetamido, etc. group), a ureido group (such as a ureido group, N-arylureido (e.g., N-phenylureido, etc.), N-alkylureido (e.g., an N-ethylureido group, etc. ) etc., group), a thiourueido group (such as a thioureido, N-arylthioureido (e.g., N-phenylthioureido, etc.), N-alkylthioureido (e.g., N-ethylthioureido, etc.), etc. group), an alkyloxycarbamido group, (e.g., a methoxycarbamido, octoxycarbamido, etc., group), an aryloxycarbamido group (e.g., a phenoxycarbamido group, etc.), an alkylthiocarbamido group (e.g., a methylthiocarbamido, octylthiocarbamido, etc., group), an arylthiocarbamido group (e.g., a phenylthiocarbamido, etc., group), an anilino group (e.g., an N-phenylamino group), an N-alkylanilino group (e.g., an N-methylanilino N-ethyl-(-b 2-chloro-5-tetradecanamido)anilino, etc. group), and N-arylanilino group (e.g., an N-phenylamino, N-phenylanilino, etc., group), and N-acyanilino group (e.g., a 2-chloro-5-tetradecanamidoanilino, etc., group), an N-alkylamino group (e.g., an N-butylamino, N-methylamino etc., group), an N,N-dialkylamino group (e.g., an N,N-dibutylamino, etc., group,), an N-cycloalkyamino group (e.g., an N-cyclohexylamino etc., group), a cycloamino group (e.g., a piperidino, pyrrolidino, etc. group), an alkylcarbonyl group (e.g., a methylcarbonyl, etc., group), an arylcarbonyl group (e.g., a phenylcabonyl, etc., group), a sulfonamido group (such as an alkylsulfonamido (e.g., methylsulfonamido, etc.), arylsulfonamido (e.g., phenylsulfonamido, etc.) group) a carbamoyl group (such as an N-alkylcarbamoyl group (e.g., N-methylcarbamoyl, N-{3-[(2,4-di-tert-amylphenoxy)acetamido]phenyl}carbamoyl, etc.,), N,N-dialkylcarbamoyl (e.g., N-methyl-N-octadecylcarbamoyl, etc.), N-alkyl-N-arylcarbamoyl (e.g., an N-methyl-N-phenylcarbamoyl, etc.,),N,N-diarylcarbamoyl (e.g., N,N-diphenylcarbamoyl etc.) etc., group), a sulfamoyl group (such as an N-alkylsulfamoyl (e.g., N-methylsulfamoyl, N- 3-[(2,4-di-tert-amylphenoxy)-acetamido]phenyl sulfamoyl, etc.,),N,N-dialkylsulfamoyl (e.g., N-methyl-N-octadecylsulfamoyl, etc.), N-arylsulfamoyl group (e.g., N-phenylsulfamoyl, etc. ), N-alkyl-N-arylsulfamoyl (e.g., N-methyl-N-phenylsulfamoyl, etc.) N,N-diarylsulfamoyl (e.g., N,N-diphenylsulfamoyl, etc.) etc., group., a guanidino group (such as an N-alkylguanidino (e.g., N-methylguanidino, etc.), N-arylguanidino (e.g., N-phenylguanidino, etc.) etc., group), a cyano group, an acyloxy group (e.g., a tetradecanoyloxy, etc., group,), a sulfonyloxy group (e.g., a benzenesulfonyloxy etc., group), a hydroxyl group, a mercapto group, a halogen atom (e.g., a chlorine, bromine, fluorine, etc. atom), or a sulfo group.

In the above-described formulae, T represents a hydrogen atom, or has up to 40, preferably up to 22, carbon atoms. Suitable examples of groups for T include a straight chain or branched chain alkyl group, an alkenyl group, a cycloalkyl group, an aralkyl group, or a cycloalkenyl group as defined for W, in which the groups may have one or more substituents as illustrated above in regard to the substituted alkyl group of W.

Furthermore, T represents also an aryl group or a heterocyclic group, each as defined for W, in which each of these groups may have one or more substituents as described above in regard to W.

Still further, T represents a cyano group, an alkoxy group (e.g., a methoxy, butoxy, octyloxy, etc., group) an aryloxy group (e.g., a phenoxy, tolyloxy, naphthoxy, etc., group), a halogen atom (e.g., a chlorine, bromine, fluorine, etc. atom), a carboxyl group, and alkoxycarbonyl group (e.g., a methoxycarbonyl, butoxycarbonyl, etc. group) an aryloxycarbonyl group,(e.g., a phenoxycarbonyl, tolyloxycarbonyl, etc., group), an acyloxy group (e.g., an acetoxy, etc., group), an alkylcarbonyl group (e.g., a methylcarbonyl, octylcarbonyl, etc., group), an arylcarbonyl group (e.g., a phenylcarbonyl, tolycarbonyl, etc., group), a thioacyl group (such as an alkylthiocarbonyl group (e.g., an ethylthiocarbonyl etc., group) an arylthiocarbonyl group (e.g., a phenylthiocarbonyl, etc., group), a sulfo group, a sulfamoyl group (e.g., a methylsulfamoyl, diethylsulfamoyl, phenylsulfamoyl, etc., group), a carbamoyl group (such as an alkylcarbamoyl , dialkylcarbamoyl, etc. group, (e.g., N-ethylcarbamoyl, N-methyl-N-decylcabamoyl, N-phenylcabamoyl, etc, group), an acylamino group (e.g., an acetamido, butyramido, benzamido, etc. group), a diacylamino group (e.g., a phthalimido, 3-heptadecylsuccinimido, etc., group), a ureido group (e.g., an ethylureido, phenylureido, chlorophenylureido, etc., group), a thioureido group (e.g., an ethylthioureido, phenylthioureido, chlorophenylthioureido, etc., group) an alkyloxycarbamido group (e.g., a methoxycarbamido, octoxycarbamido, etc., group), an aryloxycabamido group (e.g., a phenoxycarbamido etc., group), an alkylthiocarbamido group (e.g., a methylthiocarbamido, octylthiocarbamido, etc., group), an arylthiocarbamido group (e.g., a phenylthiocarbamido, etc. group), a sulfonamido group (such as an alkylsulfonamido (e.g., methylsulfonamido, ethylsulfonamido, etc.), arylsulfonamido (e.g., phenylsulfonamido, etc.) etc., group), an alkylsulfonyloxy group (e.g., an ethylsulfonyloxy, dodecylsulfonyloxy, etc., group), an arylsulfonyloxy group (e.g., a phenylsulfonyloxy, tolysulfonyloxy, etc., group), an arylsulfonyl group (e.g., a phenylsulfonyl, tolylsulfonyl, etc., group), an alkylsulfonyl group (e.g., a methylsulfonyl, octylsulfonyl, etc., group), an arylthio group (e.g., a phenylthio, tolylthio, etc., group), an alkylthio group (e.g., a methylthio, octylthio, dodecylthio, etc., group), an alkylsulfinyl group (e.g., a methylsulfinyl, hexylsulfinyl, etc., group), an arylsulfinyl group (e.g., a phenylsulfinyl, tolylsulfinyl, etc. group), an alkylamino group (e.g., a methylamino, butylamino, etc., group), a dialkylamino group (e.g., an N,N-diethylamino, N-methyl-N-decylamino, etc., group), an anilino group, an N-arylanilino group (e.g., an N-phenylanilino, etc., group), an N-alkylanilino group (e.g., an N-methylanilino etc., group), an N-acylanilino group (e.g., a 2-chloro-5-tetradecanamidoanilino etc., group), a hydroxyl group, or a mercapto group.

In the above-described general formulae, Y has up to 40 carbon atoms and represents an alkyl group, an aryl group, or a heterocyclic group as defined for W.

Suitable examples of alkyl groups for Y include a straight chain alkyl group, a branched chain alkyl group and an alkenyl group (such as a methyl, ethyl, isopropyl, allyl, hexenyl, pentadecyl, octadecyl, tert-butyl, etc., group), an aralkyl group (such as a benzyl, phenethyl, γ-phenylpropyl, etc., group), a cykloalkyl group (e.g., a cyclopentyl, and a cyclohexyl, etc., group), and a cycloalkenyl group (e.g., a cyclopentenyl, a cyclohexenyl, etc., group). Each of these groups can be substituted with one or more substituents such as a halogen atom, a nitro group, a cyano group, an aryl group, an alkoxy group, an aryloxy group, a carboxyl group, an alkylcarbonyl group, an arylcarbonyl group, an alkoxycarbonyl group, an aryloxycarbonyl group, a sulfo group, a sulfamoyl group, a carbamoyl group, an acylamino group, a diacylamino group, a ureido group, a thioureido group, a sulfonamido group, a heterocyclic group (e.g., a pyridyl group, a quinolyl group, a furyl group, a piperidyl group etc.), an arylsulfonyl group, an alkylsulfonyl group, an arylsulfonyloxy group, and alkylsulfonyloxy group, an arylthio group, an alkylthio group, an alkylsulfinyl group, an arylsulfinyl group, and a substituted amino group (e.g., an N,N-diethylamino group, etc.) as defined for the substituents of the alkyl group of W.

Examples of aryl groups represented by Y include a phenyl group, an α-naphthyl group, a β-naphthyl group, and a substituted aryl group, such as a substituted phenyl group, a substituted α-naphthyl group, and a substituted β-naphthyl group, in which these substituted aryl groups may have one or more substituents such as an alkyl group, an aralkyl group, an alkenyl group, a cycloalkyl group, a cycloalkenyl group, a halogen atom, a nitro group, a cyano group, an aryl group, an alkoxy group, an aryloxy group, a carboxyl group, an alkylcarbonyl group, an arylcarbonyl group, an alkoxycarbonyl group, an aryloxycarbonyl group, a sulfo group, an acyloxy group, a sulfamoyl group, an N,N-dialkylsulfamoyl group, an N-alkyl-N-arylsulfamoyl group, an N-alkylsulfamoyl group an N-arylsulfamoyl group, a carbamoyl group, an N-alkylcarbamoyl group, an N,N-dialkylcarbamoyl group, an N-alkyl-N-arylcarbamoyl group, an N-arylcarbamoyl group, an acylamino group, a diacylamino group, a ureido group, a thioureido group, a sulfonamido group, an alkoxycarbamido group, an aryloxycarbamido group, an alkylthiocarbamido group, an arylthiocarbamido group, a heterocyclic group (e.g., a pyridyl group, a quinolyl group, a furyl group, a piperidyl group, etc.), an alkylsulfonyl group, an arylsulfonyl group, a alkylthio group, an arylthio group, an alkylsulfinyl group, an arylsulfinyl group, and a substituted amino group (e.g., an N,N-dialkylamino group, an anilino group, a N-acylanilino group, and an N-arylanilino group), as defined for the substituents of the aryl group of W.

Furthermore, the heterocyclic groups represented by Y include a nitrogen-containing heterocyclic group (e.g., a pyridyl group, a quinolyl group, a pyrrolidyl group and a heterocyclic ring containing two or more nitrogen atoms such as a benzoimidazolyl group, and each of these groups or rings can have one or more substituents as illustrated above in regard to the aryl group of W), an oxygen-containing heterocyclic group (e.g., a tetrahydrofuryl group, a benzofuryl group, and each of these groups can have one or more substituents as illustrated above in regard to the aryl group of W), a sulfur-containing heterocyclic ring (e.g., a thienyl group, a benzothienyl group, and each of these groups can have one or more substituents as described above in regard to the aryl group of W), and a heterocyclic group having two or more different hetero atoms in the heterocyclic ring (e.g., a benzoxazolyl group, a benzothiazolyl group, etc.).

In the above-described formulae, Z represents a hydrogen atom, an alkyl group, an aryl group, or a heterocyclic group and the alkyl group, the aryl group and the heterocyclic group have the same meaning as in the case of Y. Y preferably represents a hydrogen atom or the above-described alkyl group or aryl group.

In the above-described general formulae, n represents 1 or 2.

In the above formulae, D represents an oxygen atom, a sulfur atom or an —NR— group connecting the —CO— moiety and the Y group but when n is 2, D can be a Y group, i.e., Y may be connected directly to the carbonyl group. Also, R of the —NR— group represents a hydrogen atom, an alkyl group, or an aryl group, as defined for W.

Further, Q of —N<Q represents a non-metal atomic group necessary for forming a 5-membered or 6-membered nitrogen-containing heterocyclic group. Preferred examples of heterocyclic groups are residues or pyrrolidine, piperidine, morpholine, imidazole, benzimidazole, phthalimide, succinimide, glutarimide, hydantoin, oxazolidione, benzotriazole, α-pyridone, β-pyridone, oxazolidone, valerolactam, butyrolactam, thiohydantoin, tetrazole, pyrazole, indole, imidazoline, pyrazololine, pyrazoline, piperazine, indoline, isoindoline, etc., rings.

In the couplers of this invention represented by general formulae (II), (III), (IV), and (V) any one of the, W, X, Y, and T groups in the formulae can be a divalent group to, in each case, form a symmetric or asymmetric composite coupler.

Cp—W′—Cp   (VIa)

wherein W′ represents a divalent moiety of the groups hereinbefore described for W; and Cp, which may be of the same or different, each represents a moiety of the general formulae (IIa) and (IVa)

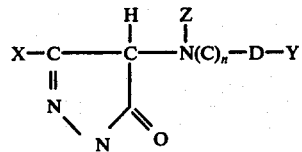
(IIa)

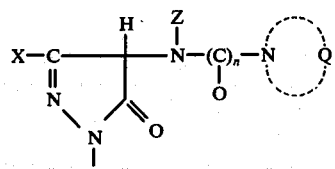
(IVa)

wherein X, Y, Z, D, —N⏜Q and n are as hereinbefore described;

Cp—X′—Cp   (VIb)

wherein X′ represents a divalent moiety of the groups hereinbefore described for X; and Cp, which may be same or different, each represents a moiety of the formulae (IIb), (IIIa), (IVb) or (Va)

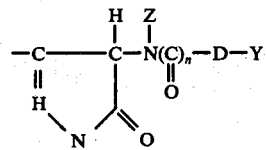
(IIb)

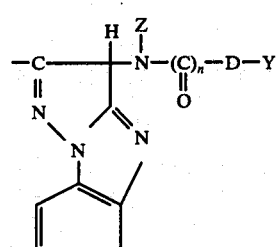
(IIIa)

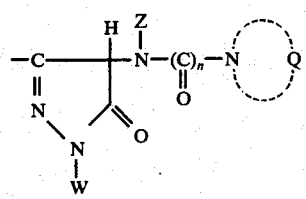
(IVb)

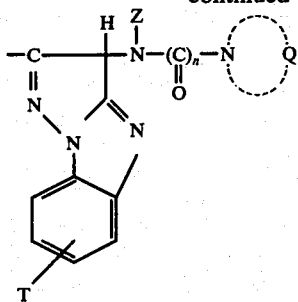
(Va)

wherein T, W, Y, Z, D, —N⏜Q and n are as hereinbefore described;

Cp—Y′—Cp   (VIc)

wherein Y′ represents a divalent moiety of the groups hereinbefore described for Y; and Cp, which may be the same or different, each represents a moiety of formula (IIc) or (IIIb)

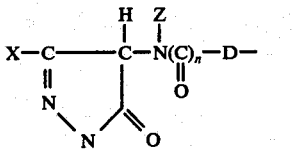
(IIc)

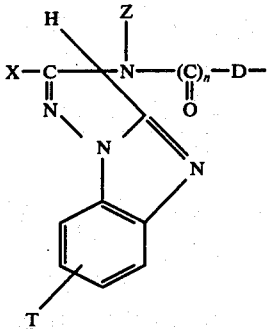
(IIIb)

wherein T, W, X, Z, D, —N⏜Q, and n are as hereinbefore described;

Cp—T′—Cp   (VId)

wherein T′ represents a divalent moiety of the groups hereinbefore described for T; and Cp, which may be the same or different, each represents a moiety of the formula (IIIc) or (Vb)

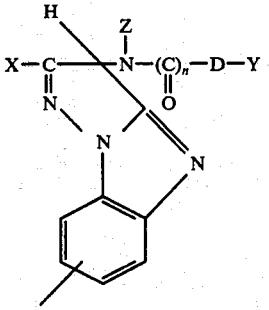
(IIIc)

-continued

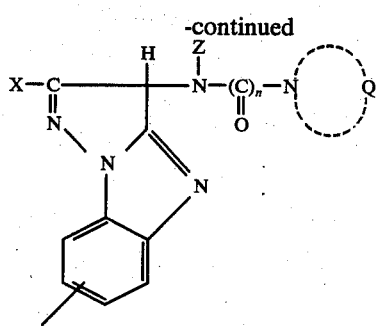
(Vb)

wherein X, Y, Z, D, —N Q, and n are as hereinbefore described.

The magenta couplers used in this invention have various desired properties depending on the embodiment or the kind of substituents for the W, X, Y, and —N Q groups and thus they can be used for various photographic purposes.

When the coupler contains a hydrophobic residue having more than 8 carbon atoms in at least one of the W, X, Y, T, and —N Q moieties, the coupler associates in a hydrophilic collid and thus the coupler becomes non-diffusible in a hydrophilic colloid layer of a colorphotographic material. Such a magenta coupler can be incorporated in a silver halide photographic emulsion of a color photographic material. Furthermore, a magenta coupler containing a diffusion resisting hydrophobic residue at the —Y or —N Q moiety and containing a water solubilizing group such as a sulfo group or a carboxyl group in at least one of the W, X, and T moieties is essentially non-diffusible but a diffusible dye is formed by the oxidative coupling reaction with a primary aromatic amino developing agent. Such a diffusible dye providing coupler is useful for diffusion transfer color photography.

The formation of dye images by the oxidative coupling of couplers and a primary aromatic amino developing agent can be classified into two modes according to the system for adding the couplers. In one of the modes the couplers are incorporated in photographic emulsion layers during the production of the color photographic materials. On the other hand, in another mode, the couplers are incorporated in the color developer and are supplied by diffusion into the photographic silver halide emulsion layers of a color photographic material at development.

The couplers used in the former mode must be fixed in the photographic emulsion layer. That is to say, they must be non-diffusible in the photographic emulsion layers of a color photographic material since if the couplers are diffusible in the photographic emulsion layers, the couplers transfer through the photographic emulsion layers and coupling occurs in other photographic emulsion layers having different color sensitivities than that of the photographic emulsion layers originally containing the couplers reducing greatly the color reproducibility of the color photographic material.

To render a coupler non-diffusible or diffusion resistant, a group having a hydrophobic residue of 8 to 32 carbon atoms is introduced into the coupler molecule. Such a residue is termed "ballast" group. The ballast group can be connected to the skeletal structure of the coupler directly or through an imino bond, an ether bond, a carbonamido bond, a sulfoamido bond, a ureido bond, an ester bond, an imido bond, a carbamoyl bond, a sulfamoyl bond, etc. Several examples of ballast groups are described in the specific examples of the magenta couplers of this invention described hereinafter.

Specific examples of ballast groups are illustrated below:

I. Alkyl groups and alkenyl groups:
For instance, —$CH_2$—$CH(C_2H_5)_2$, —$C_{12}H_{25}$, —$C_{16}H_{33}$, —$C_{17}H_{35}$, etc.

(II). Alkoxyalkyl groups:
For instance, —$(CH_2)_3$

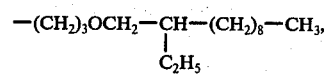

etc. as described in Japanese Patent Publication No. 27563/1964.

(III). Alkylaryl groups:

For instance, 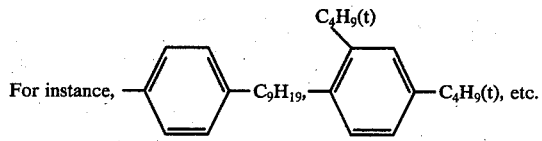, etc.

(IV). Alkylaryloxyalkyl groups:

For instance, 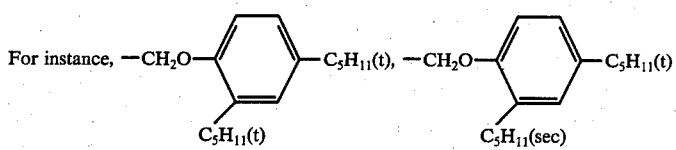

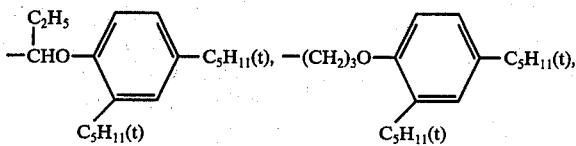

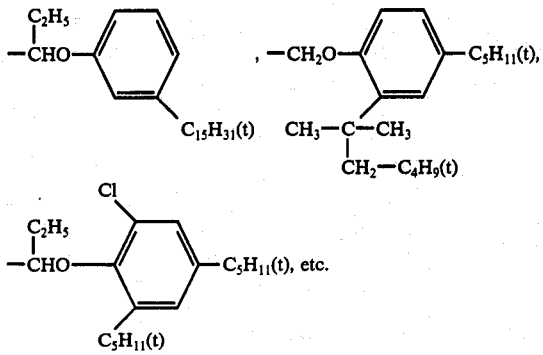

(V). Acylamidoalkyl groups:

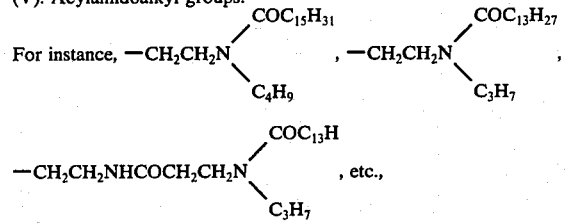

as described in U.S. Pat. No. 3,337,344 and 3,418,129.

(VI). Alkoxyaryl groups and aryloxyaryl groups:
For instance,

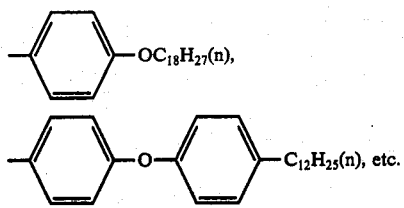

(VII). Residues having a long chain alkyl or alkenyl aliphatic group and also a carboxyl or sulfo water-solubilizing group:

For instance, 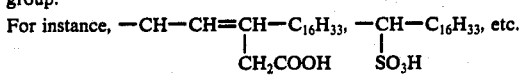

(VIII). Alkyl groups substituted with an ester group:
For instance, 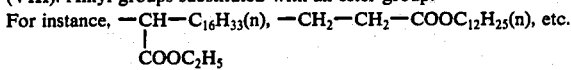

(IX). Alkyl groups substituted with an aryl group or a heterocyclic group: For instance,

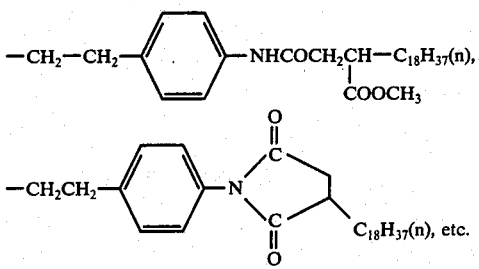

(X). Aryl groups substituted with an aryloxyalkoxycarbonyl group:
For instance,

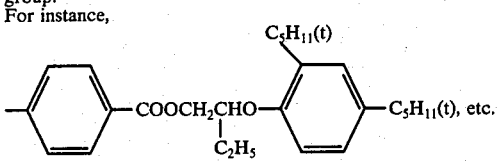

The coupler of this invention can be advantageously added to a photographic emulsion as a solution thereof in a high boiling organic solvent which has a boiling point higher than about 170° C and which is immiscible with water, a low-boiling organic solvent, a water-soluble organic solvent, a mixture of a high-boiling organic solvent immiscible with water and a low-boiling organic solvent, or a mixture of a low-boiling organic solvent and a water-soluble organic solvent.

The high-boiling organic solvents immisicible with water as described in U.S. Pat. No. 2,322,027 can be used as the solvents for the above purpose. Preferred examples of solvents are di-n-butyl phthalate, benzyl phthalate, triphenyl phosphate, tri-o-cresyl phosphate, diphenyl mono-o-chlorophenyl phosphate, mono-phenyl di-o-chlorophenyl phosphate, dioctyl phthalate, dibutyl sebacate, acetyltributyl citrate, tri-t-octyl trimellitate, n-nonyl phenol, dioctylbutyl phosphate, N, N-diethylaurylamide, 3-pentadecylphenyl ethyl ether, 2,5-di-sec-amylphenyl butyl ether, etc.

Examples of the low-boiling organic solvents having a boiling point of lower than about 170° C or water soluble organic solvents which can be used together with or in place of the high-boiling organic solvents are described in U.S. Pat. Nos. 2,801,171; 2,801,170 and 2,949,360. These organic solvents are as follows:

1. Low-boiling organic solvents substantially insoluble in water, such as methyl acetate, ethyl acetate, propyl acetate, isopropyl acetate, butyl acetate, ethyl propionate, sec-butyl alcohol, ethyl formate, butyl formate, nitromethane, nitroethane, carbon tetrachloride, chloroform, etc.

2. Water soluble organic solvents such as methyl isobutyl ketone, α-ethoxyethyl acetate, Carbitol acetate (diethylene glycol monoacetate), methoxy triglycol acetate, acetyl acetone, diacetone alcohol, butyl carbitol, methyl carbitol, methyl ethyl ketone, methanol, ethanol, acetonitrile, dimethylformamide, dioxane, etc.

The proportion of water present in the solvent solution of the coupler must be sufficiently low to avoid any adverse influence of the water on the solubility of the coupler. Further, the low-boiling or water-soluble organic solvent can be removed from the dispersion by air drying the dispersion after cooling or by continuous water washing as described in U.S. Pat No. 2,801,171.

Also, for dispersing an oil-soluble coupler, a homogenizer for emulsification, a colloid mill, ultrasonic emulsifier, etc., can be advantageously used. A non-diffusible coupler having a carboxyl group or a sulfo group together with a ballast group in the same molecule thereof is soluble in a neutral or weakly alkaline aqueous solution. Thus, the coupler can be incorporated in the photographic emulsion by adding an aqueous solution of the coupler to a photographic emulsion. It is believed that the coupler is rendered non-diffusible due to the formation of micelles in a hydrophilic polymer.

Specific examples of magenta couplers of this invention are illustrated below although this invention is not to be construed as being limited to these couplers.

Coupler (1)

N-[[1-(2,4,6-Trichlorophenyl)-3-{3-[α-(2,4-di-tert-amylphenoxy) butyramido]benzamido}-5-oxo-2-pyrazolin-4-yl]]-ethyl carbamate.

Coupler (2)

N-{1-(2,4,6-Trichlorophenyl)-3-[3-(2,4-di-tert-amylphenoxylacetamido) benzamadio]-5-oxo-2-pyrazolin-4yl}phenyl carbamate.

Coupler (3)

N-[1-(2,4,6-Trichlorophenyl)-3-(2-chloro-5-tetradecaneamidoanilino)-5-oxo-2-pyrazolin-4-yl]tolyl carbamate.

Coupler (4)

N-[[1-(2,4,6-Trichlorophenyl)-3-{2-chloro-5-[γ-(2,4-di-tert-amylphenoxy)propylsulfamoyl]anilino}-5-oxo-2-pyrazolin-4-yl]]α-naphthyl carbamate.

Coupler (5)

N-[1-(2,4-Dichloro-6-methylphenyl)-3-(3,5-dicarboxyanilino)-5-oxo-2-pyrazolin-4-yl]octadecyl oxamate.

Coupler (6)

N-[[-1-(2,4,6-Trichlorophenyl)-3-{3-α-(2,4-di-tert-amylphenoxy)butyramido]}-5-oxo-2-pyrazolin-4-yl]]ethyl oxamate.

Coupler (7)

N-[1-(2,4,6-Trichlorophenyl)-3-(2,4-dichloroanilino)-5-oxo-2-pyrazolin-4-yl](3-pentadecylphenyl) carbamate.

Coupler (8)

N-[[1-{4-α-(2,4-Di-tert-amylphenoxy)butyramido]-phenyl}-3-(2-chloroanilino)-5-oxo-2-pyrazolin-4-yl]]-S-tert-butylthio carbamate.

Coupler (9)

N-[1-(2,4,6-Trichlorophenyl)-3-methoxy-5-oxo-2-pyrazolin-4-yl]ethyl carbamate.

Coupler (10)

N-[1-Phenyl-3-methyl-5-oxo-2-pyrazolin-4-yl]ethyl oxamate.

Coupler (11)

1-(2,4,6-Trichlorophenyl)-3-[[3-{3-[α-(2,4-di-tert-amylphenoxy)butyramido]phenyl}ureido]]-4-(pentachlorophenylureido)-5-oxo-2-pyrazoline.

(12)

1-(2,4,6-Trichlorophenyl)-3-{3-[(2,4-di-tert-amylphenoxy)-acetamido]benzamadio}-4-(N-imidazolylcarboamido)-5-oxo-2-pyrazoline.

Coupler (13)

N-[[2-}3-[α-(2,4-Di-tert-amylphenoxy)butyramido]-benzamido}3H-pyrazolo-[1,5a]-benzaimidazol-3-yl]]n-pentylcarbamate.

Coupler (14)

N-(2-n-Heptadecyl-3H-pyrazolo-[1, 5a]-benzimidazol-3-yl) tert-butyloxamate.

Coupler (15)

N-{1-(2,4,6-Trichlorophenyl)-3-[3-(2,4-di-tert-amylphenoxyacetamido)benzamido]-5-oxo-2-pyrazolin-4-yl}-2-pyridylcarbamate.

Coupler (16)

N-[[1-(2,4,6-Trichlorophenyl)-3-{3-[α-(3-n-pentadecylphenoxy)butyramido]}-5-oxo-2-pyrazolin-4-yl]] phenyloxamate.

Coupler (17)

N-{1-[4-(2,4-Di-tert-amylphenoxyacetamido)phenyl]-3-(2,4-dichloroanilino-5-oxo-2-pyrazolin-4yl} (5-quinolyl)oxamate.

Coupler (18)

N-[1-(2,6Dichloro-4-methylphenyl)-3-(2,4-dichloroanilino)-5-oxo-2-pyrazolin-4-yl](5-pentadecyl)-benzofurylcarbamate.

Coupler (19)

N-Methyl-N-{1-(2,4,6-trichlorophenyl)-3-[3-(2,4-di-tert-amylphenoxyacetamido)benzamido]-5-oxo-2-pyrazolin-4-yl}phenylcarbamate.

Coupler 20)

N-[1-(2,4,6-Trichlorophenyl)-3-(3,5-dicarboxyanilino)-5-oxo-2-pyrazolin-4-yl]-S-octadecylthiooxamate.

Coupler (21)

N-[1-(2,6-Dichloro-4-methoxyphenyl)-3-(2-chloro-5-N-methylsulfamoylanilino)-5-oxo-2-pyrazolin-4-yl]-S-(4-hydroxy-3-n-pentadecylphenoxy)ethyl carbamate.

The magenta coupler of this invention can be prepared by reacting a magenta coupler having an amino group at the coupling position and a cabonic acid halide derivative or an oxalic acid halide derivative according to the reaction schematic shown below:

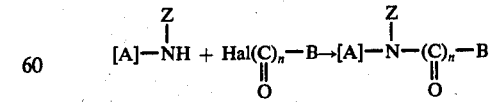

wherein n, Z, and B have the same significance as defined above, "Hal" represents a halogen atom such as a chlorine atom, [A] represents a four equivalent magenta dye-forming coupler as defined above, and a

means that the coupling position has been substituted, i.e., replacing one of the hydrogen atoms of the active methylene group.

Since the magenta coupler having an amino group at the coupling position, which is used as a starting material for preparing the magenta coupler of this invention is generally unstable in a neutral condition and is readily oxidized to form a yellow dye or orange dye, it is advantageous to convert the starting material into a stable strong acid salt (e.g., hydrochloride or sulfate), a stannic chloride salt and such a salt can be easily used for the above-described reaction. For instance, 4-amino-5-oxo-2-pyrazoline coupler can be prepared by the method as described in U.S. Pat. No. 3,419,391. Namely, the two-equivalent magenta coupler can be easily obtained by nitrosolating the 4-position of a four-equivalent coupler, 5-oxo-2-pyrazoline with an appropriate nitroosolating agent such as, for instance, sodium nitrite, isoamyl nitrite etc. and then reducing the nitrosolation product in an appropriate manner (e.g., by a hydrogenation with hydrogen using a catalyst such as palladium-carbon, etc., or by a chemical reduction using stannous chloride, etc.).

The reaction of a 4-amino-5-oxo-2-pyrazoline and a carbonic acid halide derivative or a oxalic acid halide derivative as shown in the above-described reaction schematic can be performed in a solvent which is inert to the carbonic acid halide derivative or the oxalic acid halide derivative at a temperature of from about 0° C to about 100° C but it is preferred to carry out the reaction is a protic polar solvent such as a carboxylic acid solvent (e.g., acetic acid, propionic acid, etc.), a halogenated hydrocarbon solvent (e.g., methylene chloride, chloroform, carbon tetrachloride, etc.,), benzene, pyridine, quinoline, dimethylformamide, dimethyl sulfoxide, etc., at a temperature of from about 0° C to about 40° C.

Furthermore, in the reaction, it is preferred to use an appropriate hydrogen halide accepting agent as the catalyst and triethylamine, diazobicyclo[2,2,2]octane, and sodium acetate can be effectively used as the catalyst.

Moreover, to inhibit the production of colored dyes as by-products from the starting material, 4-amino-5-oxo-2-pyrazoline, as much as possible, it is preferred to control slowly the rate of addition of the above-described hydrogen halide accepting agent and further to conduct the reaction under an inert gas such as nitrogen gas. Also, the pyrazolobenzimidazoles represented by above general formulae (III) and (V) as well as other magenta couplers of this invention can be also prepared in a similar manner.

The following examples are given to illustrate a few typical embodiments of producing the two-equivalent magenta couplers of this invention. Unless otherwise indicated herein, all parts, percentages, ratios and the like are by weight.

SYNTHESIS EXAMPLE 1

Production of N-{1-(2,4,6-Trichlorophenyl)-3[3-(2,4di-tert-amylphenoxyacetamido)benzamido]-5-oxo-2-pyrazoline-4-yl}-phenylcarbamate, (Coupler 2):

In 50 ml of chloroform was dissolved 3.7 g of 1-(2,4,6-trichlorophenyl)-3-{3-[(2,4-di-tert-amylphenoxy)acetamido]benzamido}-4-amino-5-oxo-2-pyrazoline stannic chloride salt (described in U.S. Pat. No. 3,419,391) and then 800 mg of phenyl chlorocarbonate was added dropwise to the solution. Then, after slowly adding dropwise a solution of 0.5 g of triethylamine in 20 ml of chloroform to the mixture, the resultant mixture was stirred at 10°-30° C. The dropping rate of the solution was so controlled that the reaction mixture did not become deep orange. After the reaction was over, the chloroform was removed under a reduced pressure and after adding 100 ml of ethyl acetate to the residue, the mixture was washed repeatedly with water. The ethyl acetate solution thus formed was dried over anhydrous sodium sulfate, concentrated, and the product in the solution was crystallized from a mixture of hexane and ethyl acetate in a 10:1 by volume ratio to provide 2.4 g of Coupler (2) having a melting point of 125°-130° C.

Elemental Analysis for $C_{41}H_{42}N_5O_6Cl_3$: Calculated: H: 5.24% C: 61.0% N: 8.68%; Found: H: 5.20% C: 61.12% N: 8.66%.

SYNTHESIS EXAMPLE 2

Production of N-[[1-(2,4,6-Trichlorophenyl)-3-{3-[α-(2,4-di-tert-amylphenoxy)butyramido]benzamido}-5-oxo-2-pyrazolin-4-yl]]ethyloxamate, (Coupler 6):

In 100 ml of chloroform was dissolved 7.5 g of 1-(2,4,6-trichlorophenyl)-3-{3-[α-(2,4-di-tert-amylphenoxy)butyramido]-benzamido}-4amino-5-oxo-2-pyrazoline stannic chloride salt (prepared by the method shown in U.S. Pat. No. 3,419,391) and then 1.4 g of ethyl chloroxalate was added dropwise to the solution. Then, a solution of 1.1 g of triethylamine in 20 ml of chloroform was slowly added dropwise to the mixture. By treating the resultant mixture as in Example 1 and then crystallizing the product from a mixture of hexane and ethyl ether in a 20:1 by volume ratio, 4.8 g of Coupler (6) having a melting point of 104°-110° C was obtained.

Elemental analysis for $C_{40}H_{46}N_5O_7Cl_3$: Calculated: H: 5.65% C: 59.0% N: 8.60%; Found: H: 5.63% C: 60.1% N: 8.61%.

The two-equivalent magenta couplers of this invention are clearly different from the above described conventional two-equivalent magenta couplers in chemical structure. Furthermore, the couplers of this invention are chemically stable and also can be easily prepared as will be understood from the above-described examples.

The coupler of this invention is a two-equivalent coupler. That is to say, the coupler of this invention requires stoichiometrically only two equivalents of silver halide as an oxidizing agent for forming 1 mole of dye.

Thus, since the coupler of this invention requires about ½ of the amount of silver halide required in the case of using a conventional four-equivalent pyrazolone type coupler, in using the coupler of this invention, the amount of silver halide incorporated in color photographic materials can be reduced by one-half, which results in reducing the cost of producing the color photographic materials as well as reducing the occurrence of light scattering due to the silver halide grains to improve the sharpness of color images.

Also, the magenta coupler used in this invention can be converted into an azomethine dye in a high yield by an oxidative coupling reaction using exposed silver halide as the oxidizing agent. With some kinds of conventional four-equivalent couplers side-reactions of the leuco dyes which are intermediate products of the dyes such as the formation of an azine ring occur to reduce the conversion thereof to dyes. On the other hand, such a reactive intermediate product is not formed with the coupler used in this invention and hence the coupler can be converted into an azomethine dye in a high yield. Therefore, in the color photographic material containing the magenta forming coupler of this invention, the amount of the coupler can be reduced, which enables a reduction in the amount of silver halide and in the thickness of the silver halide emulsion layers. This results in a reduction of the cost of the color photographic materials, an improvement in the sharpness of color images, and facilitating a speed up of the development procedure.

The magenta coupler used in this invention has a strong coupling reactivity to the oxidized primary aromatic amino color developing agent and hence the oxidation product of the developing agent formed at color development is removed quickly, which results in promoting the development of the silver halide emulsion layers of the color photographic material.

In using the magenta coupler of this invention, the dye image formation is finished in the color developer bath and the color photographic material thus developed can then be processed in a blix bath containing a weak oxidizing agent such as a ferric chelate of ethylenediamine tetraacetic acid and a silver complex salt forming agent or a ferric salt such as ferric chloride without need of a bleach bath containing a strong oxidizing agent such as potassium ferricyanide or potassium dichromate, thus shortening the period of time required for finishing all processing steps of the color development and minimizing the pollution problems caused by disposal of waste solutions.

The magenta coupler having a substituent at the coupling position used in this invention is inactivated to a lesser extent by the action of carbonyl compounds such as an aldehydes and ketones. On the other hand, a conventional coupling position unsubstituted magenta coupler is converted into a compound having a low coupling reactivity such as a methylol compound or a methylene bis compound in the photographic emulsion layer by the action of formaldehyde, etc., present in the surrounding environment and thus such a conventional coupler frequently does not exhibit sufficient coloring on color development. One of the important features of the color photographic material of this invention containing the excellent magenta coupler of this invention is that the photographic material is influenced to a lesser extent by the substances as mentioned above.

When the coupling position substituted magenta coupler of this invention is used in a color photographic material having a conventional configuration as described in the examples of this invention shown below, the coupler present in the photographic emulsion layers is stable for a long period of time and less reduction in the coupling activity of the coupler occurs when the color photographic material is exposed to a comparatively low temperature and high humidity condition for a long period of time as compared with the above-described known magenta couplers. The stability of the unexposed color photographic films in the case of storage for a long period of time is one of the important factors for evaluating the qualities of color photographic materials. Furthermore, the color images formed form the magenta coupler of this invention are remarkably superior in heat fastness to conventional coupler-position unsubstituted magenta couplers and the color images are also superior in heat fastness to the color images formed from the above-described known magenta couplers having a substituent at the 4-position of the same pyrazolone nucleus.

The two-equivalent magenta coupler of this invention can be used together with the magenta couplers in which the amount of these other magenta couplers employed with the two equivalent magenta couplers of the invention, in general, ranges from about 5 to 80 mole % based on the total amount of the magenta couplers employed, as described in, for instance, U.S. Pat. Nos. 2,439,089; 2,369,489; 2,600,788; 3,558,319; 2,311,081; 3,419,391; 3,214,437; 3,006,759; 2,725,292; 3,408,194; 2,908,573; 3,519,429; 3,615,506; 3,432,521; 3,152,896; 3,062,653; 3,582,322; 2,801,171; 3,311,476; British Patent No. 956,261; Japanese Patent Publication Nos. 2016/1969 and 19032/1971; Japanese Patent Application Nos. 114445/1972; 56050/1973; 45971/1973; 21454/1973; 108798/1973; and 114446/1972, the magenta-colored couplers incorporated in an amount from about 2 to 20 mole % to the total amount of the magenta couplers employed, as described in U.S. Pat. Nos. 2,983,608; 2,455,170; 2,725,292; 3,005,712; 3,519,429; and 2,688,539; British Patent Nos. 800,262 and 1,044,778; and Belgian Patent No. 676,691, the so-called development inhibitor releasing type couplers capable of imagewise releasing development inhibiting compounds at development, generally incorporated in an amount from about 2 to 20 mole % to the total amount of the magenta couplers employed, such as, for instance, the monothio type couplers as described in U.S. Pat. Nos. 3,227,550 and 3,227,554 and British Patent No. 953,454, the o-aminophenylazo type couplers as described in U.S. Pat. No. 3,148,062, and the couplers as described in Japanese Patent Publication No. 8750/1972 and German Patent Application (OLS) No. 2,163,811, and also the hydroquinone releasing development inhibiting compounds which can be employed therewith in an amount from about 2 to 20 mole % to the total amount of the magenta couplers employed as described in U.S. Pat. No. 3,297,445 and British Patent No. 1,058,606.

Two or more kinds of the above described magenta couplers can be incorporated in a same silver halide photographic emulsion layer to achieve the characteristics required for the color photographic materials or the same kind of coupler can, of course, be incorporated in two or more different silver halide emulsion layers depending on the purpose of the color photographic material. The magenta coupler of this invention is generally coated together with the silver halide photographic emulsion at a coverage of about $1 \times 10^{-4}$ to $5 \times 10^{-3}$ mole/m², preferably $3 \times 10^{-4}$ to $2 \times 10^{-3}$ mole/m².

In another embodiment of this invention, the magenta coupler of this invention is incorporated in a color developer. In this case the amount of the coupler is about 0.2 g to 50 g, preferably 0.5 g to 10 g per liter of the developer.

The magenta coupler of this invention is preferably used with a green-sensitive silver halide emulsion of a color photographic material.

It is advantageous for the color photographic material of this invention to contain a p-substituted phenol derivative for improving the light fastness of the magenta dye formed in the silver halide emulsion layer or an adjacent layer and also for preventing the occurence of yellowing, print out, and color stains caused by the coupler remaining in the unexposed areas after developing the silver halide photographic material. Particularly effective examples of p-substituted phenol derivatives are the hydroquinone derivatives as described in U.S. Pat. Nos. 2,360,290; 2,418,613; 2,675,314; 2,701,197;

2,704,713; 2,710,801; 2,728,659; 2,732,300; 2,735,765; 2,816,028; etc., the gallate derivatives as described in U.S. Pat. Nos. 3,457,079 and Japanese Patent Publication No. 13496/1968, the p-alkoxyphenols as described in U.S. Pat. No. 2,735,765 and Japanese Patent (OPI) No. 4738/1972, and the p-oxyphenol derivatives as described in U.S. Pat. Nos. 3,432,300; 3,573,050; and 3,574,627 and Japanese Patent Application No. 121454/1970.

The silver halide emulsion used in this invention can be prepared by mixing an aqueous solution of a water-soluble silver salt such as silver nitrate and an aqueous solution of a water-soluble halide such as potassium bromide in the presence of a water-soluble polymer such as gelatin. Examples of suitable silver halides are silver chloride, silver bromide, silver chlorobromide, silver iodobromide, silver chloroiodobromide, etc. These sivler halide grains can be prepared according to any conventional manner and a so-called single jet system, double jet system, or control double jet system can of course be employed.

Also, two or more silver halide emulsions prepared separately can be mixed to produce a silver halide emulsion. Furthermore, the silver halide grains used in this invention can have a uniform crystal structure throughout the entire grain or have a layer structure wherein the interior has a different structure than that of the outer portion of the grain. Furthermore, the silver halide grains can be the so-called conversion type silver halide grains as described in British Patent No. 635,841 and U.S. Pat. No. 3,622,318. Moreover, the silver halide grains can be the type wherein a latent image is mainly formed on the surface of the grains or the type wherein a latent image is mainly formed in the interior of the grains. These silver halide photographic emulsions can be prepared by various methods, such as an ammonia method, a neutralization method, an acid method, etc.

The silver halide emulsion used in this invention can be chemically sensitized. Examples of the chemical sensitizers which can be used for the purpose are, for instance, gold compounds such as auric acid chloride, gold trichloride, etc., as described in U.S. Pat. Nos. 2,399,083; 2,540,085; 2,597,856; and 2,597,915, salts of noble metals such as platinum, palladium, iridium, rhodium, ruthenium, etc., as described in U.S. Pat. Nos. 2,448,060; 2,540,086; 2,566,245; 2,566,263; 2,598,079, etc., sulfur compounds capable of forming silver sulfite by reaction with silver salts as described in U.S. Pat. Nos. 1,544,944; 2,410,698; 3,189,458; and 3,501,313, and stannous salts, amines and other reductive materials as described in U.S. Pat. Nos. 2,487,850; 2,518,698; 2,421,925; 2,521,026; 2,694,637; 2,983,610 and 3,201,254.

The hydrophilic colloids which can be used as the vehicle for the silver halide in this invention include gelatin, colloidal albumin, casein, carboxymethyl cellulose, hydroxyethyl cellulose, agar agar, sodium alginate, starch derivatives, synthetic hydrophilic colloids, e.g., polyvinyl alcohol, poly-N-pyrrolidone, polyacrylic acid copolymers, polyacrylamide and the derivatives and the partially hydrolized products thereof. If desired, a mixture of two or more these colloids which are compatible with each other can be used. Of the above-described colloids, gelatin is most generally used but a part or all of the gelatin can be replaced with a synthetic polymer. Furthermore, a so-called gelatin derivative, that is to say, gelatin modified by treating the gelatin with a compound having a group of capable reacting with the functional groups of the gelatin molecule, i.e., an amino group, an imino group, a hydroxyl group, and a carboxyl group or also a graft polymer of gelatin formed by bonding the molecular chain of another polymer to the gelatin can be substituted for a part or all of the gelatin.

The silver halide photographic emulsion used in this invention can be subjected to a spectral sensitization or dye sensitization using cyanine dyes such as cyanine, merocyanine, carbocyanine dyes individually or as a combination thereof. These dye sensitization techniques are well known as disclosed in U.S. Pat. Nos. 2,688,545; 2,912,329 ; 3,397,060; 3,615,635; 3,628,964; British Patent Nos. 1,195,302; 1,242,588; and 1,293,862, German Patent Application (OLS) Nos. 2,030,326 and 2,121,780, and Japanese Patent Publication Nos. 4936/1968 and 14030/1969. They can be selected appropriately according to the wave length region to be sensitized, the sensitivity desired and the purposes and uses of the color photographic materials.

Furthermore, various additives can be further added to the above-described photographic emulsions for preventing a reduction in sensitivity of the color photographic materials and a formation of fog during the production, storage, and processing of the color photographic materials.

These additives include 4-hydroxy-6-methyl-1,3,3a7-tetraazaindene, 3-methylbenzothiazole, 1-phenyl-5-mercaptotetrazole as well as many other heterocyclic compounds, mercury-containing compounds, mercapto compounds, and metal salts.

The silver halide emulsion further can be hardened using conventional methods. Hardening agents which can be used include aldehyde compounds such as formaldehyde, glutaraldehyde, etc.; ketone compounds such as diacetyl and cyclopentadione; bis(2-chloroethylurea); 2-hydroxy-4,6-dichloro-1,3,5-triazine; compounds having reactive halogens as described in U.S. Pat. Nos. 3,288,775 and 2,732,303 and British Patent Nos. 974,723 and 1,167,207; divinyl sulfone, 3-acetyl-1,3-diacryloylhexahydro-1,3,5-triazine; and also the various compounds described in U.S. Pat. Nos. 3,635,718 and 3,232,763; British Patent No. 994,869; and U.S. Pat. Nos. 2,732,316; 2,586,168; 3,103,437; 3,017,280; 2,983,611; 2,725,294; 2,725,295; 3,100,704; 3,091,537; 3,321,313; and 3,543,292.

The above-described silver halide emulsions can further contain surface active agents, either individually or a mixture thereof. These surface agents can be used as coating aids, dispersing agents, and sensitizers as well as for improving the photographic characteristics, static prevention, and adhesion prevention. These surface active agents include natural surface active agents such as saponin, etc.; nonionic surface active agents such as alkylene oxides, glycerins, glycidols, etc.; anionic surface active agents such as higher alkylamines, quaternary ammonium salts, pyridine, other heterocyclic compounds, phosphoniums, and sulfoniums; and amphoteric surface active agents such as aminoacids, aminosulfonates, sulfuric acid esters or phosphoric acid esters of aminoalcohols, etc.

Some specific examples of surface active agents which can be used in this invention are illustrated in U.S. Pat. Nos. 2,271,623; 2,240,472; 2,288,226; 2,739,891; 3,068,101; 3,158,484; 3,201,253; 3,210,191; 3,294,540; 3,415,649; 3,441,413; 3,442,654; 3,475,174; and 3,545,974, German Patent Application (OLS) No. 1,942,665, and British Patent Nos. 1,077,317 and 1,198,450.

When the present invention is applied to multilayer color photographic materials, open-chain type diketomethylene compounds are generally used as yellow couplers. These compounds are described in, for instance, U.S. Pat. Nos. 3,341,331; 3,253,924; 3,384,657; 2,778,658; 2,908,573; 3,227,550; 2,875,057; 3,551,155, German Patent Application (OLS) No. 1,547,868, U.S. Pat. Nos. 3,265,506; 3,582,322; and 3,725,072, German Patent Application (OLS) Nos. 2,162,899, U.S. Pat. Nos. 3,369,895; 3,227,155; 3,447,928; 3,415,652; and 3,408,194, and German Patent Application (OLS) Nos. 2,057,941; 2,213,461; 2,219,917; 2,261,361; and 2,263,875. Typical examples of suitable yellow couplers which can be used include the following couplers materials. Examples of such derivatives are described in, for instance, U.S. Pat. Nos. 2,369,929; 2,474,293; 2,908,573; 3,619,196; 3,253,294; 3,227,550; 3,419,390; 3,476,563; 2,698,794; 2,895,826; 3,311,476; 3,458,315; 2,423,730; 2,801,171; 3,046,129; 3,516,831; 2,772,162; 33,560,212; 3,582,322; 3,591,383; 3,386,301; 3,632,347; 3,652,286; 3,779,763; 2,434,272; 2,706,684; 3,034,892; 3,583,971; German Patent Application (OLS) Nos. 2,163,811 and 2,207,468, Japanese Patent Publication Nos. 28836/1970 and 27563/1964, and Japanese Patent Application No. 33238/1973. Typical examples of suitable cyan couplers which can be used include the following couplers

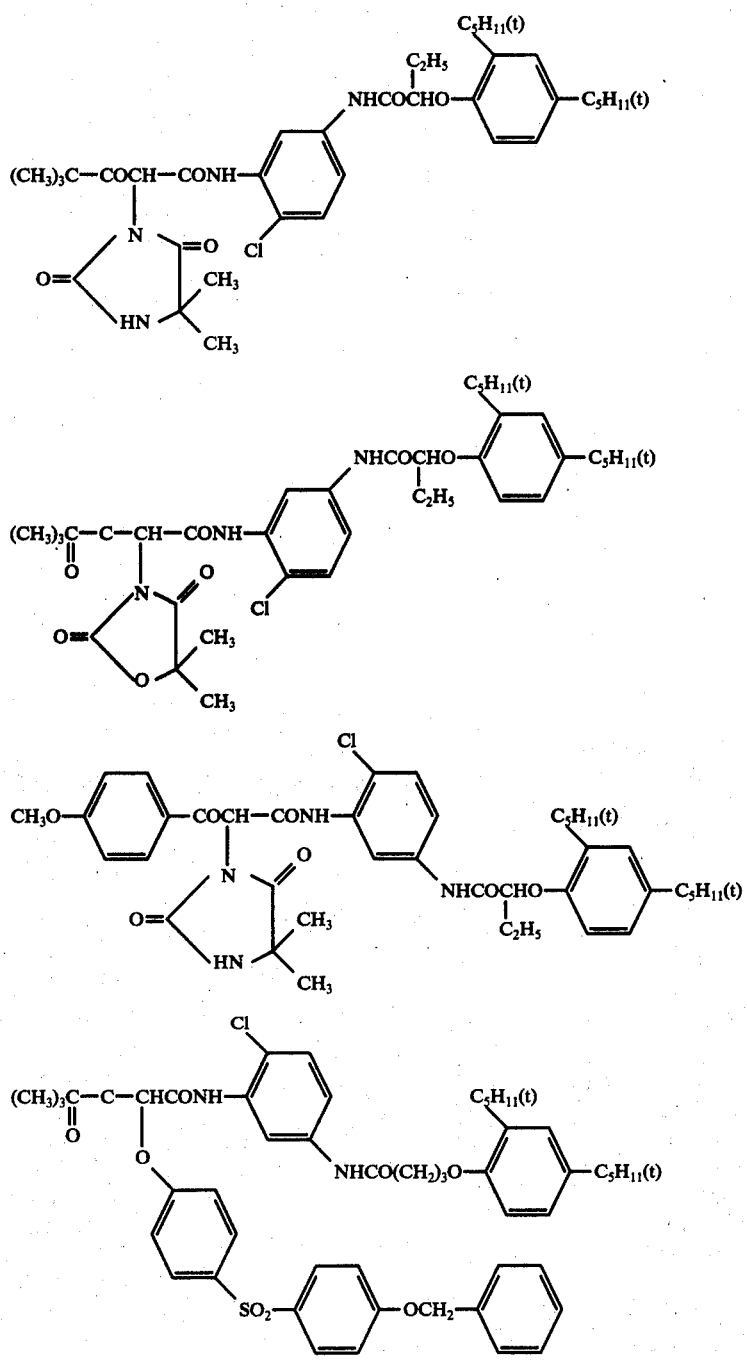

Also, phenol derivatives or naphthol derivatives are mainly used as cyan couplers for color photographic

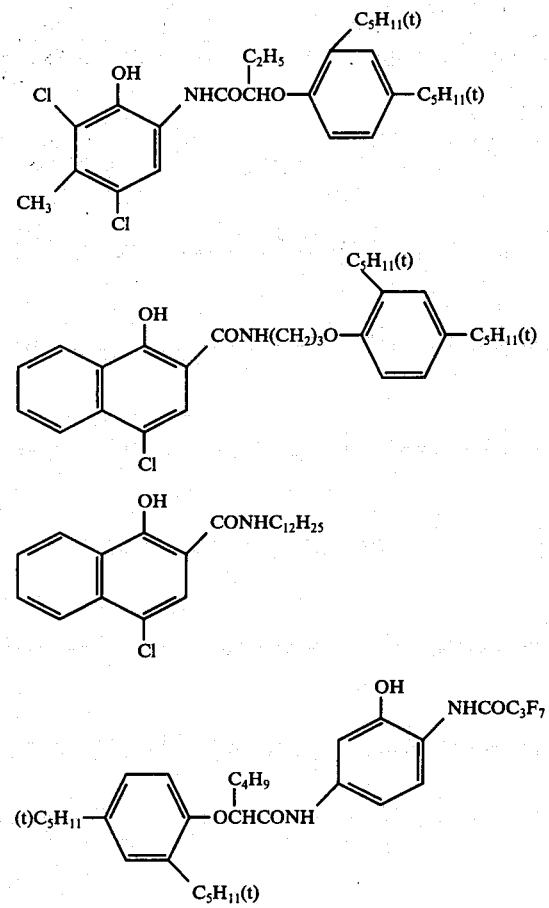

The color photographic material of this invention can contain in the protective layer, interlayers, silver halide emulsion layers, and back layer thereof the ultraviolet absorbents as described in, for instance, U.S. Pat. Nos. 2,685,512; 2,739,888; 2,784,087; 3,253,921; 3,533,794; 3,738,837; and 3,754,919.

The photographic silver halide emulsions are coated on a substantially planar material which does not undergo any substantial dimensional change during processing such as a rigid support, e.g., glass, metal and ceramics, or a flexible support. Typical examples of flexible supports are cellulose acetate films, cellulose nitrate films, cellulose acetate butyrate films, cellulose acetate propionate films, polystyrene films, polyethylene terephthalate films, polycarbonate films, laminates of these films, thin glass sheets, and papers. Furthermore, barytacoated papers and papers coated or laminated with an olefinic polymer such as, in particular, polyethylene, polypropylene, an ethylene-butene copolymer, and a polymer of an α-olefin having 2 to 10 carbon atoms can be also used as the flexible support. Also, a synthetic resin film having a roughend surface for improving the adhesive property to other polymers and improving also the printability as described in Japanese Patent Publication No. 19068/1972 can be used. These supports can be transparent or opaque according to the purpose of the photographic materials and also the transparent support can be colorless or can be colored with a dye or pigment.

Suitable opaque supports include papers which are intrinsically opaque, transparent films opacified with a dye or a pigment such as titanium oxide, the surface treated synthetic resin films as shown in Japanese Patent Publication No. 19068/1972, and papers and synthetic resin films which were rendered completely light-shielding by adding carbon black or dyes. When the adhesion between the support and the silver halide photographic emulsion layer is insufficient, a layer having high adhesion to the both the support and the emulsion layer can be formed on the support as a subbing layer. Also, for improving the adhesion of the support, the surface of the support can be pre-treated with, for instance, a corona discharge, ultraviolet radiation, a flame treatment, etc. A suitable silver halide coating amount in one emulsion layer can range from about $5 \times 10^{-5}$ to $10^{-6}$ mole/m$^2$.

In order to obtain dye images of the color photographic material of this invention, the color photographic material is developed after imagewise exposure. The development process includes fundamentally a color development step, a bleach step, and a fixing step. In this case, each step can be applied independently or two or more of these steps can be performed together using a processing solution with these functions. For instance, the bleach step and the fix step can be carried out in one step using a blix bath. Furthermore, each step can be, if desired, carried by as two or more steps or further the development process can be carried out using the combination of a color development step, a first fixing step, and blixing step. Furthermore, the development process can include further, if desired, a prehardening bath, a neutralization bath, a first development (black & white development), a image stabilization bath, and a washing. The processing temperature is determined appropriately according to the kind of photographic materials and the processing steps and sometimes the temperature is lower than about 18° C but usually is higher than about 18° C. Ordinary processing temperatures are about 20° to 60° C and recently about 30° to 60° C. In addition, it is not always necessary to carry out the all of the processing steps at the same temperature.

The color developer used for the development is an alkaline aqueous solution containing a developing agent of which the oxidation product forms a dye-forming compound by reaction with a coupler and having a pH of higher than about 8, preferably a pH of 9 to 12.

The above-described color developing agent is a compound having a primary amino group and the ability to develop exposed silver halide or a precursor thereof capable of forming such a compound. Typical examples of suitable developing agents are 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 4-amino-3-methyl-N-ethyl-N-β-methanesulfonamidoethylaniline, 4-amino-N,N-diethylaniline, 4-amino-3-methoxy-N,N-diethylaniline, 4-amino-3-methyl-N-ethyl-N-β-methoxyethylaniline, 4-amino-3-methoxy-N-ethyl-N-β-methoxyethylaniline, 4-amino-3-methanesulfoamidoethyl-N,N-diethylaniline, and the salts (e.g., sulfates, hydrochlorides, sulfites, p-toluenesulfonates, etc.) of them. Other examples of developing agents are described in U.S. Pat. Nos. 2,193,015 and 2,592,364, Japanese Patent Application (OPI) No. 64933/1973, and L. F. A. Mason, *Photographic Processing Chemistry*, pages 226–229, Focal Press, London, (1966). Also, the above described compounds can be used together with 3-pyrazolidones.

The color developer can, if desired, contain various additives. Main examples of these additives are alkalis (e.g., the hydroxides, carbonates, and phosphates of alkali metals and ammonia), pH controlling agents or buffers (e.g., weak acids such as acetic acid and boric acid, weak bases, and the salts thereof), development accelerators (e.g., the pyridinium compounds and cationic compounds as described in U.S. Pat. Nos. 2,648,604 and 3,671,247; potassium nitrate and sodium nitrate; the polyethylene glycol condensates and the derivatives thereof as described in U.S. Pat. Nos. 2,533,990; 2,577,127 and 2,950,970; nonionic compounds such as polyethio ethers as described in British Patent No. 1,020,032; polymers containing a sulfite ester group as described in U.S. Pat. No. 3,068,097; organic amines such as pyridine and ethanolamine; benzyl alcohol; and hydrazines), antifoggants (e.g., alkali metal bromides; alkali metal iodides; nitrobenzoimidazoles, 5-methylbenzotriazoles, and 1-phenyl-5-mercaptobenztriazoles as described in U.S. Pat. Nos. 2,496,940 and 2,656,271; compounds for rapid processing as described in U.S. Pat. Nos. 3,113,864; 3,342,596; 3,295,976; 3,615,522; and 3,597,199; thiosulfonyl compounds as described in British Patent No. 972,211; the phenazine-N-oxides as described in Japanese Patent Publication No. 41675/1971; and the antifoggants as described in *Kagaku Shashin Binran*, 2nd Vol. pages 29–47), stain- or sludge-preventing agents as described in U.S. Pat. Nos. 3,161,513 and 3,161,514 and British Patent Nos. 1,030,442; 1,144,481; and 1,251,588, the multilayer effect promoters as disclosed in U.S. Pat. No. 3,536,487, and preservatives (e.g., sulfites, acid sulfites, hydroxyamine hydrochloride, formsulfite, alkanolamine sulfite addition products).

The silver halide photographic material is subjected to a bleach treatment in a conventional manner after the color development and the bleach treatment can be carried out separately from or simultaneously with the fix treatment. If desired, a fixing agent can be added to the bleach solution to provide a blix solution. Examples of suitable bleaching agents are ferricyanides, dichromates, water-soluble cobalt (III) salts, water-soluble copper (II) salts, water-soluble quinones, nitrosophenols, compounds of polyvalent metals such as iron (III), cobalt (III), and copper (II), the complex salts of these polyvalent metal cations and organic acids (e.g., the metal complex salts of ethylenediamine tetraacetic acid, nitrilotriacetic acid, iminodiacetic acid, N-hydroxyethyl ethylenediaminetriacetic acid, malonic acid, tartaric acid, malic acid, diglycolic acid, and dithioglycolic acid and the copper complex salt of 2,6-dipicolinic acid), peracids (e.g., alkylperacids, persulfates, permanganates, hydrogen peroxide), and hypochlorites, chlorine, bromine, etc. They can be used individually or as a mixture thereof.

Furthermore, the processing solution used for bleaching or blixing can further contain the bleach accelerators as described in U.S. Pat. Nos. 3,042,520 and 3,241,966 and Japanese Patent Publication Nos. 8506/1970 and 8836/1970.

The formation of dye images using the magenta coupler of this invention is suitable for various kinds of color photographic materials. In one embodiment, a color photographic material comprising a support having thereon a silver halide emulsion layer containing a non-diffusible coupler is processed with an alkaline developer containing a primary aromatic amino color developing agent, whereby a water-insoluble or non-diffusible dye is left in the silver halide emulsion layer. In another embodiment, a color photographic material comprising a support having thereon a silver halide emulsion layer associated with a non-diffusible coupler is processed with an alkaline developer containing a primary aromatic amino color developing agent to form a diffusible dye which is soluble in an aqueous medium and the dye image formed is transferred by imbibition to an image-receiving layer composed of a hydrophilic colloid. In a further embodiment, the coupler is dissolved in an alkaline developer containing a primary aromatic amino color developer and then by processing a color photographic material having a silver halide emulsion layer with the developer, a water-insoluble or non-diffusible dye is left in the silver halide emulsion layer. For instance, Coupler (5) and Coupler (20) illustrated above can used in the second embodiment, Coupler (9) and Coupler (10) can be used in the third embodiment, and the other couplers illustrated above can be used in the first embodiment.

The color photographic materials of this invention include color negative films, color positive films, color reversal films, color papers, etc.

Also, the present invention can be employed in other various photographic materials including color direct positive photographic materials, diffusion transfer color photographic materials, and monochromatic photographic materials.

By applying the method as described in U.S. Pat. Nos. 2,439,901; 2,623,822; 2,814,565; and 3,372,028 in which the developed silver formed by color development is subjected to a halogenation bleach and then color development again to increase the amount of the dye formed or the method as described in Japanese Patent Application (OPI) No. 9728/1973 in which the amount of silver halide in the color photographic material is reduced by a color intensifying method to the color photographic materials containing the couplers of this invention, better results can be obtained.

Some of the advantages of the invention are as follows:

1. Since the amount of silver required for specific magenta dye image density can be reduced by the use of the two-equivalent magenta coupler of this invention, the thickness of the silver halide emulsion layer containing the coupler can be reduced and further the sharpness of the color image formed can be improved.

2. The use of the magenta coupler of this invention provides a magenta dye image having improved heat fastness.

3. The cost of the color photographic materials can be reduced due to the ability to reduce the amount of silver halide used in the silver halide emulsion layers.

4. The magenta coupler of this invention is stable to chemical substances such as formaldehyde and acetone present in the surrounding environment.

5. The magenta coupler of this invention has a high development activity.

6. The color photographic material containing the magenta coupler of this invention provides a color image with less fog and stains and with other excellent photographic properties.

7. The use of the magenta coupler of this invention provides silver halide color photographic materials having high stability on storage.

8. The magenta coupler of this invention has a high conversion to the dye.

The invention will be explained more specifically by reference to the following examples.

EXAMPLE 1

A solution prepared by heating a mixture of 22.5 g of Coupler (2) shown above, 24 ml of dioctylbutyl phosphate, and 60 ml of ethyl acetate to 60° C was added to 250 ml of an aqueous solution at 60° C and containing 2.5 g of gelatin and 0.75 g of sodium dodecylbenzenesulfonate and the resultant mixture was stirred vigorously using a homogenizer to provide an emulsified dispersion of the coupler. The emulsified dispersion thus obtained was mixed with 200 g of a silver halide photographic emulsion containing $11.2 \times 10^{-2}$ mole of silver chlorobromide (45 mole% silver bromide, 55 mole% silver chloride) and 20 g of gelatin and after adding thereto 10 ml of a 3% acetone solution of triethylene phosphoramide as a hardening agent and adjusting the pH thereof to 6.5, the mixture was coated on a cellulose triacetate film in a dry thickness of 4.5 microns to provide Film A. The photographic film contained $1.55 \times 10^{-3}$ mole of the coupler and $6.2 \times 10^{-3}$ mole of silver chlorobromide per square meter.

For comparison, 18.8 g of a comparison coupler corresponding to the aforesaid coupler but with no substituent at the coupling position, i.e., 1-(2,4,6-trichlorophenyl)-3-{3-[(2,4-di-tert-amylphenoxy)acetamido]benzamido}-5-oxo-2-pyrazoline (Comparison Coupler A) was dispersed in the manner above, the dispersion of the coupler was mixed with 400 g of the silver halide emulsion having the same composition as above, and the mixture was coated on the same kind of film support as above in a dry thickness of 5.1 microns (Film B). The comparison photographic film contained $1.57 \times 10^{-3}$ mole of the coupler and $12.6 \times 110^{-3}$ mole of silver chlorobromide per square meter.

Each of the photographic films thus prepared was exposed through a step wedge and subjected to the following development processing.

| Color Development Processing: | | |
|---|---|---|
| 1. Color Development | 21° C | 12 min. |
| 2. Wash | " | 30 sec. |
| 3. First Fix | " | 4 min. |
| 4. Wash | " | 4 min. |
| 5. Bleach | " | 8 min. |
| 6. Wash | " | 4 min. |
| 7. Second Fix | " | 4 min. |
| 8. Wash | " | 6 min. |

The compositions of the processing solutions used in the above processing were as follows:

| Color Developer: | |
|---|---|
| Sodium Hexametaphosphate | 2 g |
| Sodium Sulfite (anhydrous) | 2 g |
| Benzyl Alcohol | 5 ml |
| Sodium Carbonate (mono-hydrate) | 27.5 g |
| Potassium Bromide | 0.5 g |
| Hydroxyamine Sulfate | 2.5 g |
| N-Ethyl-N-(β-methanesulfoneamidoethyl)-3-methyl-4-amino-aniline sesquisulfate | 2.5 g |
| Water to make | 1 liter |
| Fix Solution: | |
| Sodium Thiosulfate (6H$_2$O) | 80 g |
| Sodium Sulfite (anhydrous) | 5 g |
| Borax | 6 g |
| Glacial Acetic Acid | 4 ml |
| Potassium Alum | 7 g |
| Water to make | 1 liter |
| | (pH 4.5) |
| Bleach Bath: | |
| Potassium Ferricyanide | 100 g |
| Potassium Bromide | 5 g |
| Borax | 5 g |
| Boric Acid | 10 g |
| Water to make | 1 liter |
| | (pH 7.2). |

After the processing, the optical density of each of the film samples was measured using green light and the results obtained are shown in Table 1. The film provided a sharp color image having the photographic characteristics as shown in Table 1 and having an absorption maximum at 542 mμ.

Table 1

(Photographic characteristics)

| Film | Coupler | Coupler Coated Amount (mol/m²) | AgX Coated Amount (mol/m²) | Ag/Coupler (molar ratio) | Layer Thickness (μ) |
|---|---|---|---|---|---|
| A | (2) | $1.55 \times 10^{-3}$ | $6.2 \times 10^{-3}$ | 4 | 4.5 |
| B | A | $1.57 \times 10^{-3}$ | $12.6 \times 10^{-3}$ | 8 | 5.1 |

| Film | Fog | Gamma | Relative* Sensitivity | Maximum Coupling Density |
|---|---|---|---|---|
| A | 0.03 | 3.45 | 100 | 3.51 |
| B | 0.02 | 2.19 | 89 | 2.45 |

*The reactive sensitivity was the exposure amount required for a density of fog + 0.1

The results shown in Table 1 demonstrate that when the coupler of this invention was used, a high sensitivity, a high gradation, and a high maximum coupling density were obtained as compared with the case of using the comparison coupler despite the use of a silver halide/coupler ratio which was ½ of that of the comparison case.

The above results also demonstrate that in using the coupler of this invention, the amount of the developed silver necessary for obtaining a dye image having a specific density can be reduced. That is to say, it can be understood from the above results that in using the coupler of this invention, the amounts of silver halide and coupler required for obtaining a maximum coupling density can be reduced and also the period of time required for finishing the development processing can be also shortened.

EXAMPLE 2

Film samples having the same structures as those of Film A and Film B shown in Example 1 were subjected to the following development processing:

| Color Development Processing: | | |
|---|---|---|
| 1. Color Development | 30° C | 4 min. |
| 2. Blix | 30° C | 2 min. |
| 3. Wash | 30° C | 2 min. |
| 4. Stabilization | 30° C | 2 min. |

The photographic characteristics of the films thus obtained are shown in Table 2 below.

In this case, a stabilization bath (a) which did not contain formaldehyde and a stabilization bath (b) containing 1% of a 40% formalin aqueous solution were prepared. The films thus processed were allowed to stand for 1 week at 80° C and then the reduction in density to the initial density was measured for both films. The results obtained are shown in Table 3 below.

The compositions used in the above processings were as follows:

| Color Developer: | |
|---|---|
| Sodium Metaborate | 25 g |
| Sodium Sulfite | 2 g |
| Hydroxylamine Sulfate | 2 g |
| Potassium Bromide | 0.5 g |
| 6-Nitrobenzimidazole (nitrate) | 0.02 g |
| Sodium Hydroxide | 4 g |
| Benzyl Alcohol | 15.8 ml |
| Diethylene Glycol | 20 ml |
| 4-(N-Ethyl-N-β-methanesulfoneamido-ethyl)amino-2-methylaniline Sesquisulfate | 8 g |
| Water to make | 1 liter (pH 10.2) |
| Blix Solution: | |
| Ferric Salt of Ethylenediamine-tetraacetic Acid | 45 g |
| Ammonium Thiocyanate | 10 g |
| Sodium Sulfite | 10 g |
| Ammonium Thiosulfate (60% aq. soln.) | 100 ml |
| Sodium Ethylenediamine Tetraacetate | 5 g |
| Water to make | 1 liter (pH 6.9) |
| Stabilization Bath (a): | |
| Tartaric Acid | 10 g |
| Zinc Sulfate | 10 g |
| Sodium Metaborate | 20 g |
| Water to make | 1 liter |
| Stabilization Bath (b): | |
| Tartaric Acid | 10 g |
| Zinc Sulfate | 10 g |
| Sodium Metaborate | 20 g |
| Formalin (40% aq. soln.) | 10 ml |
| Water to make | 1 liter |

| | | Photographic Characteristics (stabilization Bath (a)) | | |
|---|---|---|---|---|
| Film | Coupler | Fog | Gamma | Maximum Coupling Density |
| A | (2) | 0.04 | 3.51 | 3.55 |
| B | A | 0.03 | 2.25 | 2.35 |

Table 3

| | | Fastness of Color Image (after 1 week at 80° C) | | |
|---|---|---|---|---|
| | | | Initial Density | |
| Film | Stabilization Bath | 0.5 | 1.0 | 2.0 |
| | | (%) | (%) | (%) |
| A | | | | |
| | a | 11 | 9 | 7 |
| | b | 10 | 5 | 5 |
| B | | | | |
| | a | 60 | 41 | 11 |
| | b | 12 | 8 | 7 |

The results in Table 2 show that Film A provided sufficient photographic characteristics even if the strong oxidizing agent as in the development of Example 1 was not used and Film A had superior characteristics to those of Film B. Also, the results of Table 3 show that Film A provided color images having sufficient heat fastness even if a stabilization bath containing formaldehyde was not used.

EXAMPLE 3

A baryta-coated paper coated additionally with polyethylene films was coated with a blue-sensitive silver chlorobromide (70 mole% of silver bromide, and 30 mole% of silver chloride) containing α-pivaloyl-α-(2,4-dioxo-5,5-dimethyloxazolzolidinyl)-2-chloro-5-[α-(2,4-di-tert-amylphenoxy)butyramido]-acetanilide in a thickness of 3.0 microns and at coverage of $1.18 \times 10^{-3}$ mole/m² of the coupler, $3.53 \times 10^{-3}$ mole/m² of silver, as a first layer.

Then, an aqueous gelatin solution containing 2-t-octyl hydroquinone was coated thereon in a thickness of 1.5 microns and a coverage of 0.05 g/m² of the hydroquinone as a second layer.

Furthermore, a solution was prepared by heating a mixture of 10.8 g of Coupler (4) of this invention, 0.8 g of 6,6'-dihydroxy-7,7'-dimethyl-4,4,4',4'-tetramethyl-bis-2,2'-spirocumarone, and 10 ml of tricresyl phosphate on a steam bath was added to an aqueous solution containing 10 g of gelatin and 0.5 g of sodium cetyl sulfate followed by stirring well to provide an emulsified dispersion, the dispersion was mixed with 100 g of a silver halide photographic emulsion containing $4.7 \times 10^{-2}$ mole of silver chlorobromide (50 mole% silver chloride, 50 mole% silver bromide) and 9 g of gelatin and after adding thereto 3 ml of a 4% aqueous solution of the sodium salt of 2-hydroxy-4,5-dichloro-s-triazine as a hardening agent and controlling the pH of the mixture to 6.3, the resultant mixture was coated as a third layer in a thickness of 1.8 microns and a coverage of $4.2 \times 10^{-4}$ mole/m² of the coupler and $1.68 \times 10^{-3}$ mole/m² of silver.

Then, an aqueous gelatin solution contining 2,5-di-t-octyl hydroquinone and an ultraviolet absorbent, 2-(5-chlorobenzotriazol-2-yl)-4-methyl-6-t-butylphenol and 2-(benzotriazol-2-yl)-4-t-butylphenol was coated thereon as a fourth layer in a thickness of 2.5 microns and a coverage of 0.05 g/m² of the hydroquinone and 0.4 g/m² of the benzotriazole compounds.

Thereafter, a red-sensitive silver chlorobromide (50 mole% of silver bromide, and 50 mole% of silver chloride) emulsion layer containing 2-[α-(2,4-di-t-amylphenoxy)butyramido]-4,5-dichloro-5-methylphenol was coated thereon as a fifth layer in a thickness of 2.5 microns and a coverage of $0.98 \times 10^{-3}$ mole/m² of the coupler, $2.94 \times 10^{-3}$ mole/m² of silver.

Finally, an aqueous gelatin solution was coated as the uppermost protective layer in a thickness of 1.0 micron.

Thus, a color print paper (Color Paper C) was obtained.

For comparison, a color print paper (Color Paper D) was prepared in the same manner as above except that in forming the third layer, the emulsified dispersion of the coupler was prepared using 8.7 g of 1-(2,4,6-trichlorophenyl)-3-{2-chloro-5-[γ-(2,4-di-tert-amylphenoxy)propylsulfamoyl]anilino}-5-oxo-2-pyrazoline (Comparison Coupler B) and after mixing the dispersion with 200 g of the silver halide emulsion having the same composition as above, the mixture was coated in a dry thickness of 3.0 microns and at a coverage of $6.7 \times 10^{-4}$ mole/m² of the coupler and $5.36 \times 10^{-3}$ mole/m² of silver.

Each of the samples thus prepared was stepwise exposed, subjected to the same development procedure as above using stabilization bath (a), and the reflective density of the image obtained was measured using green light, whereby a color image having the photographic characteristics as shown in Table 4 below and an absorption maximum of 543 mμ was obtained.

Table 4

| | | (Photographic Characteristics) | | | |
|---|---|---|---|---|---|
| | | Coated Amount | | | |
| Film | Coupler | Coupler (mole/m²) | AgX (mole/m²) | AgX/Coupler (molar ratio) | Fog |
| C | (4) | $4.2 \times 10^{-4}$ | $1.68 \times 10^{-3}$ | 4 | 0.06 |
| D | B | $6.7 \times 10^{-4}$ | $5.36 \times 10^{-3}$ | 8 | 0.05 |

Table 4-continued

| Film | (Photographic Characteristics) | | Maximum Coupling Density |
|---|---|---|---|
| | Gamma | Relative Sensitivity | |
| C | 2.55 | 100 | 2.47 |
| D | 2.48 | 97 | 2.40 |

The results shown in Table 4 demonstrate that the color photographic material containing the coupler of this invention provided the same photographic characteristics as conventional color photographic materials even though the amount of silver halide was reduced.

Furthermore, after exposing the photographic film thus developed to a day light flurescent lamp of an illumination of about 30,000 lux through a ultraviolet absorbing filter which completely absorbed ultraviolet light of wavelengths shorter than 400 mµ for 12 days, the light fastness of the photograph was measured.

Also, the heat fastness of the photographic color image after allowing the material to stand for 1 week in the dark at 80° C and the moisture resistance of the photograph after storing the material for 2 weeks in the dark at a relative humidity of 75% and at 60° C were measured. These results are shown as a density reduction (%) to the initial density. The results are shown in Table 5.

Table 5

| Film | Coupler | (Fastness of Color Image) | | | | | | | | |
|---|---|---|---|---|---|---|---|---|---|---|
| | | (A)* Initial Density | | | (B)* Initial Density | | | (C)* Initial Density | | |
| | | 0.5 | 1.0 | 2.0 | 0.5 | 1.0 | 2.0 | 0.5 | 1.0 | 2.0 |
| | | (%) | (%) | (%) | (%) | (%) | (%) | (%) | (%) | (%) |
| C | (4) | 17 | 10 | 5 | 7 | 4 | 2 | 6 | 3 | 2 |
| D | B | 21 | 13 | 6 | 12 | 6 | 4 | 10 | 5 | 4 |

(A) Exposed to fluorescent lamp for 12 days.
(B) Stored for 1 week at 80° C in the dark
(C) Stored for two weeks at 60° C and 75% RH in the dark.

From the results shown in Table 5 above it can be understood that by using the coupler of this invention a color image having high fastness to heat and humidity was obtained.

While the invention has been described in detail and with reference to specific embodiments thereof, it will be apparent to one skilled in the art that various changes and modifications can be made therein without departing from the spirit and scope thereof.

What is claimed is:

1. A color photographic material comprising a support having thereon at least one silver halide emulsion layer containing a two-equivalent magenta coupler represented by the general formulae (II) to (V):

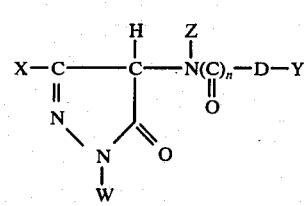

(II)

wherein W represents a hydrogen atom; or has up to 40 carbon atoms and represents a straight chain or branched chain alkyl group, an alkenyl group, a cycloalkyl group, an aralkyl group, a cycloalkenyl group, an aryl group, a heterocyclic group, an acyl group, a thioacyl group, an alkysulfonyl group, an arylsulfonyl group, an alkylsulfinyl group, an arylsulfinyl group, a cabamyl group, or a thiocarbamoyl group;

X represents a hydrogen atom; or has up to 40 carbon atoms and represents a straight chain or branched chain alkyl group, an alkenyl group, a cycloalkyl group, an aralkenyl group, a cycloalkenyl group, an aryl group, a heterocyclic group, an alkoxycarbonyl group, an aryloxycarbonyl group, an aralkyloxycarbonyl group, an alkoxy group, an aryloxy group, an alkylthio group, an arylthio group, a carboxyl group, an acylamino group, a diacylamino group, an N-alkylacylamino group, an N-arylacylamino group, a ureido group, a thioureido group, an alkoxycarbamido group, an aryloxycarbamido group, an alkylthiocarbamido group, an arylthiocarbamido group, an anilino group, an alkylamino group, a cycloamino group, an alkylcarbonyl group, an arylcarbonyl group, a sulfoamido group, a carbamoyl group, a sulfamoyl group, a guanidino group, a cyano group, an acyloxy group, a sulfonyloxy group, a hydroxyl group, a mercapto group, a halogen atom, or a sulfo group; Z represents a hydrogen atom, a alkyl group, an aryl group, or a heterocyclic group; and D represents an oxygen atom, a sulfur atom or a —N-R— group; R of the —NR— group represents a hydrogen atom, an alkyl group or an aryl group; Y represents an alkyl group, an aryl group or a heterocyclic group; n is 1 or 2

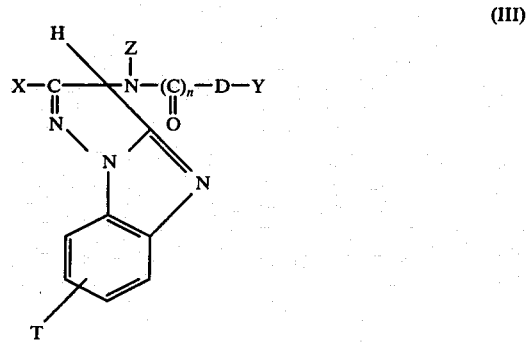

(III)

wherein X, Y, Z, D, and n are each as defined hereinbefore, and,

T represents a hydrogen atom; or has up to 40 carbon atoms and represents a straight chain or branched chain alkyl group, an alkenyl group, a cycloalkyl group, an aralkyl group, a cycloalkenyl group, an aryl group, heterocyclic group, a cyano group, an alkoxy group, an alkoxycarbonyl group, a halogen atom, an aryloxy group, a carboxyl group, an aryloxycarbonyl group, an acyloxy group, an alkylcarbonyl group, an arylcarbonyl group, an alkylthiocarbonyl group, an arylthiocarbonyl group, a sulfo group, a sulfamoyl group, a carbamoyl group, a acylamino group, a dicylamino group, a ureido group, a thioureido group, an alkoxycarbamido group, an aryloxycarbamido group, an alkylthiocarbamido group, an arythiocarbamido group, a sulfonamido group, an alkysulfonyloxy group, an arylsulfonyloxy group, an arysulfonyl group, an alkylsulfonyl group, an arylthio group, an alkylthio group, an alkylsulfinyl group, an arysulfinyl group, an alkylamino group, a dialkylamino group, an anilino group, an N-arylanilino group, a N-alkylanilino group, an N-acylanilino group, a hydroxyl group, or a mercapto group;

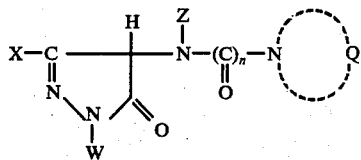
(IV)

wherein Q is the —N͡Q residue represents a nonmetal atomic group necessary for forming a 5-membered or 6-membered nitrogen-containing heterocyclic group and wherein W, X, Z, and n are each as defined hereinbefore;

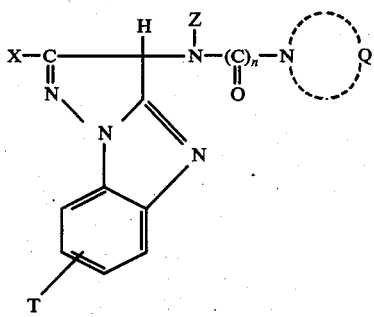
(V)

Wherein X, Z, T, —N͡Q, and n are each as defined hereinbefore; or represented by the general formulae (VIa) to (VId)

, Cp — W' — Cp (VIa)

wherein W' represents a divalent moiety of the groups hereinbefore described for W; and Cp, which may be the same or different, each represents a moiety of the general formulae (IIa) and (IVa)

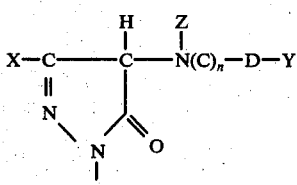
(IIa)

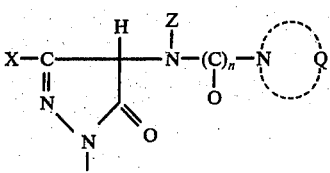
(IVa)

wherein X, Y, Z, D, —N͡Q and n are as hereinbefore described;

Cp — X' — Cp (VIb)

wherein X' represents a divalent moiety of the groups hereinbefore described for X; and Cp, which may be the same or different, each represents a moiety of the formula (IIb), (IIIa), (IVb) or (Va)

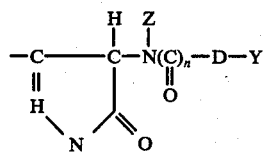
(IIb)

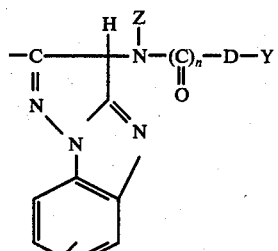
(IIIa)

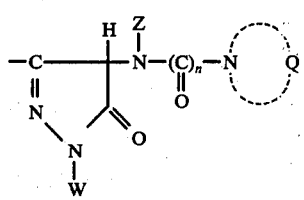
(IVb)

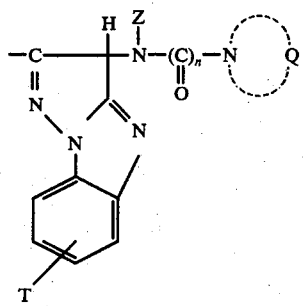
(Va)

wherein T, W, Y, Z, D, —N͡Q and n are as hereinbefore described;

Cp — Y' — Cp (VIc)

wherein Y' represents a divalent moiety of the groups hereinbefore described for Y; and Cp, which may be the same or different, each represents a moiety of formula (IIc) or (IIIb)

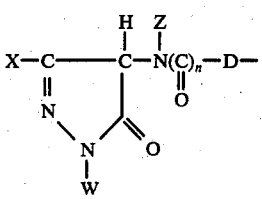
(IIc)

-continued (IIIb)

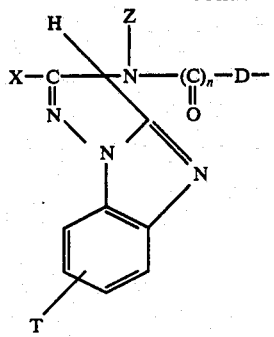

Wherein T, W, X, Z, D, —N⋯Q, and n are as hereinbefore described;

Cp — T' — Cp     (VId)

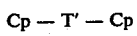

wherein T' represents a devalent moiety of the groups hereinbefore described for T; and Cp, which may be the same or different, each represents a moiety of the formula (IIIc) or (Vb)

(IIIc)

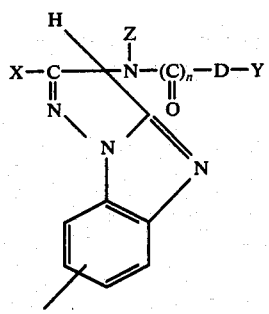

(Vb)

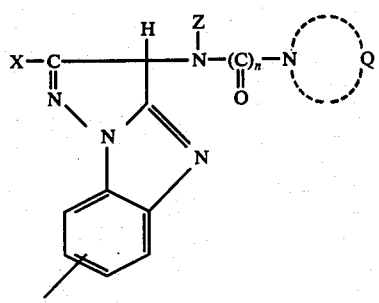

wherein X, Y, Z, D, —N⋯Q, and n are as hereinbefore described.

2. The color photographic meterial as set forth in claim 1, in which said silver halide emulsion layer containing the magenta coupler is a green-sensitive silver halide emulsion layer.

3. The process of forming color images which comprises processing an exposed color photographic material comprising a support having thereon at least one silver halide emulsion layer with a color developer containing a primary aromatic amino color developing agent in the presence of a two-equivalent magenta coupler represented by the general formulae (II) to (V):

(II)

-continued (IIIb)

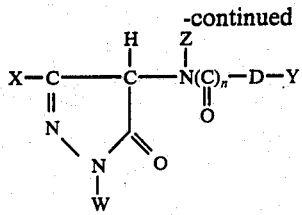

wherein W represents a hydrogen atom; or has up to 40 carbon atoms and represents a straight chain or branched chain alkyl group, an alkenyl group, a cycloalkyl group, an aralkyl group, a cycloakenyl group, an aryl group, heterocyclic group, an acyl group, a thioacyl group, an alkylsulfonyl group, an arylsulfonyl group, an alkylsulfinyl group, an arylsulfinyl group, a carbamyl group, or a thiocarbamoyl group;

X represents a hydrogen atom; or has up to 40 carbon atoms and represents a straight chain or branched chain alkyl group, an alkenyl group, a cycloalkyl group, an aralkenyl group, a cycloalkenyl group, an aryl group, a heterocyclic group, an alkoxycarbonyl group, an aryloxycarbonyl group, an aralkyloxycarbonyl group, an alkoxy group, an aryloxy group, an alkylthio group, an arylthio group, a carboxyl group, an acylamino group, a diacylamino group, an N-alkylacylamino group, an N-arylacylamino group, a ureido group, a thioureido group, an alkoxycarbamido group, an aryloxycarbamido group, an alkythiocarbamido group, an arylthiocarbamido group, an anilino group, an alkylamino group, a cycloamino group, an alkycarbonyl group, an arylcarbonyl group, a sulfoamido group, a carbamoyl group, a sulfamoyl group, a guanidino group, a cyano group, an acyloxy group, a sulfonyloxy group, a hydroxyl group, a mercapto group, a halogen atom, or a sulfo group; Z represents a hydrogen atom, a alkyl group, an aryl group, or a heterocyclic group; and D represents an oxygen atom, a sulfur atom or a —NR— group; R of the —NR— group represents hydrogen atom, an alkyl group or an aryl group; Y represents an alkyl group, an aryl group or a heterocyclic group; n is 1 or 2

(III)

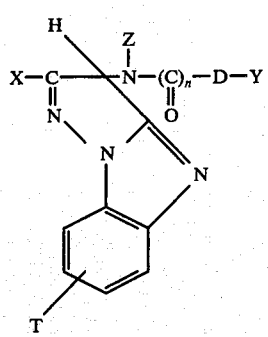

wherein X, Y, Z, D, and n are each as defined hereinbefore, and,

T represents a hydrogen atom; or has up to 40 carbon atoms and represents a straight chain or branched chain alkyl group, an alkenyl group, a cycloalkyl group, an aralkyl group, a cycloalkenyl group, an aryl group, a heterocyclic group, a cyano group, an alkoxy group, an alkoxycarbonyl group, a halogen atom, an aryloxy group, a carboxyl group, an aryloxycarbonyl group, an acyloxy group, an alkylcarbonyl group, an arylcarbonyl group, an alkylthiocarbonyl group, an arylthiocarbonyl group, a sulfo group, a sulfomoyl group, a carbamoyl group, an acylamino group, a diacylamino group, a ureido group, a thioureido group, an alkoxycarbamido group, an aryloxycarbamido group, an alkythiocarbamido group, an arythiocarbamido group, a sulfonamido group, an alkysulfonyloxy group, an arylsulfonyloxy group, an arylsulfonyl group, an alkylsulfonyl group, an arylthio group, an alkylthio group, an alkylsulfinyl group, an arysulfinyl group, an alkylamino group, a dialkylamino group, an anilino group, an N-arylanilino group, a N-alkylanilino group, an N-acylanilino group, a hydroxyl group, or a mercapto group;

(IV)

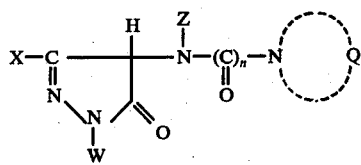

wherein Q of the —N⋯Q residue represents a nonmetal atomic group necessary for forming a 5-membered or 6-membered nitrogen-containing heterocyclic ring and
wherein W, X, Z, —N⋯Q, and n are each as defined hereinbefore;

(V)

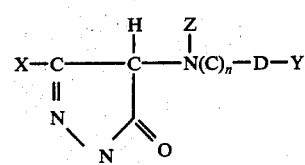

wherein X, Z, T, —N⋯Q, and n are each as defined hereinbefore; or represented by the general formulae (VIa) to (VId)

Cp — W' — Cp    (VIa)

wherein W' represents a divalent moiety of the groups hereinbefore described for W; and Cp, which may be the same or different, each represents a moiety of the general formulae (IIa) and (IVa)

(IIa)

X—C———C—N(C)$_n$—D—Y (IVa)

-continued

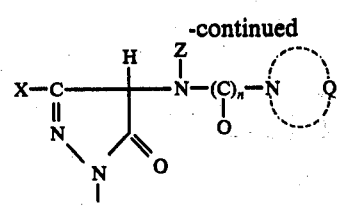

wherein X, Y, Z, D, —N⋯Q and n are as hereinbefore described

Cp — X' — Cp    (VIb)

wherein X' represents a divalent moiety of the groups hereinbefore described for X; and Cp, which may be the same or different, each represents a moiety of the formula (IIb), (IIIa), (IVb) or (Va)

(IIb)

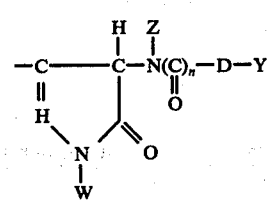

(IIIa)

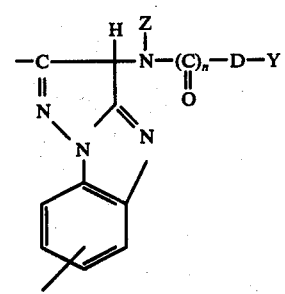

(IVb)

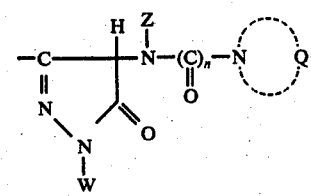

(Va)

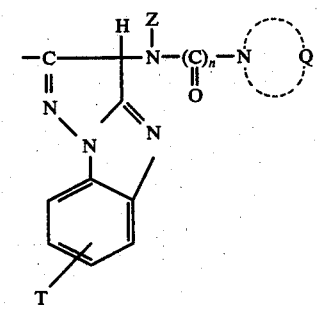

wherein T, W, Y, Z, D, —N⋯Q and n are as hereinbefore described;

Cp — Y' — Cp    (VIc)

wherein Y' represents a divalent moiety of the groups hereinbefore described for Y; and Cp, which may be the same or different, each represents a moiety of formula (IIc) or (IIIb)

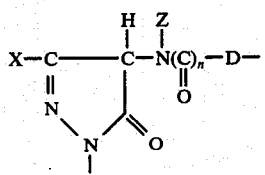 (IIc)

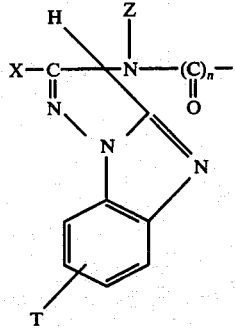 (IIIb)

wherein T, W, X, Z, D, —N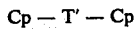Q, and n are as hereinbefore described;

Cp — T' — Cp        (VId)

wherein T' represents a divalent moiety of the groups hereinbefore described for T; and Cp, which may be the same or different, each represents a moiety of the formula (IIIc) or (Vb)

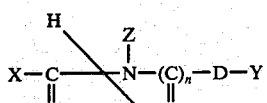 (IIIc)

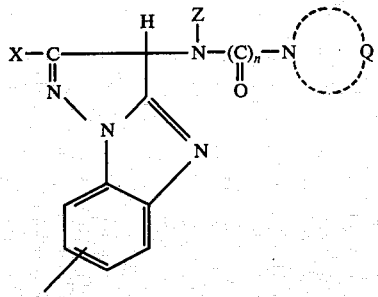 (Vb)

wherein X, Y, Z, D, —N Q, and n are as hereinbefore described.

4. The color image-forming process as set forth in claim 3, in which said two-equivalent magenta coupler is present in the color photographic material.

5. The color image-forming process as set forth in claim 3, in which said two-equivalent magenta coupler is present in the color developer.

* * * * *